US 8,039,488 B2
Oct. 18, 2011

(12) United States Patent
D'Amato

(10) Patent No.: US 8,039,488 B2
(45) Date of Patent: *Oct. 18, 2011

(54) METHODS AND COMPOSITIONS FOR INHIBITION OF ANGIOGENESIS

(75) Inventor: Robert J. D'Amato, Cambridge, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/249,847

(22) Filed: Oct. 10, 2008

(65) Prior Publication Data

US 2009/0036412 A1 Feb. 5, 2009

Related U.S. Application Data

(63) Continuation of application No. 11/411,230, filed on Apr. 26, 2006, now Pat. No. 7,435,745, which is a continuation of application No. 09/287,377, filed on Apr. 7, 1999, now abandoned, which is a continuation of application No. 08/963,058, filed on Nov. 3, 1997, now abandoned.

(60) Provisional application No. 60/028,708, filed on Nov. 5, 1996.

(51) Int. Cl.
*A61K 31/445* (2006.01)
(52) U.S. Cl. ..................................... 514/323
(58) Field of Classification Search ............. 514/323
See application file for complete search history.

(56) References Cited

U.S. PATENT DOCUMENTS

| | | |
|---|---|---|
| 2,830,991 A | 4/1958 | Keller et al. |
| 3,560,495 A | 2/1971 | Frankus |
| 3,563,986 A | 2/1971 | Frankus |
| 3,625,946 A | 12/1971 | Heinrich et al. |
| 3,705,162 A | 12/1972 | Graudums et al. |
| 4,552,888 A | 11/1985 | Koppel et al. |
| 4,808,402 A | 2/1989 | Leibovich et al. |
| 4,994,443 A | 2/1991 | Folkman et al. |
| 5,001,116 A | 3/1991 | Folkman et al. |
| 5,021,404 A | 6/1991 | Folkman et al. |
| 5,134,127 A | 7/1992 | Stella et al. |
| 5,260,329 A | 11/1993 | Mongelli et al. |
| 5,385,901 A | 1/1995 | Kaplan et al. |
| 5,399,363 A | 3/1995 | Liversidge et al. |
| 5,405,855 A | 4/1995 | Andrulis, Jr. |
| 5,434,170 A | 7/1995 | Andrulis, Jr. |
| 5,443,824 A | 8/1995 | Piacquadio |
| 5,502,066 A | 3/1996 | Heinemann |
| 5,605,684 A | 2/1997 | Piacquadio |
| 5,605,914 A | 2/1997 | Muller |
| 5,629,327 A | 5/1997 | D'Amato |
| 5,643,915 A | 7/1997 | Andrulis, Jr. et al. |
| 5,654,312 A | 8/1997 | Andrulis, Jr. et al. |
| 5,679,696 A | 10/1997 | Fenton et al. |
| 5,731,325 A | 3/1998 | Andrulis, Jr. et al. |
| 6,140,346 A | 10/2000 | Andrulis, Jr. et al. |
| 7,435,745 B2 * | 10/2008 | D'Amato ............... 514/323 |

FOREIGN PATENT DOCUMENTS

| | | |
|---|---|---|
| EP | 1182709 | 3/1970 |
| EP | 0325199 | 7/1989 |
| EP | 0357061 | 3/1990 |
| WO | WO 91/10424 | 7/1991 |
| WO | WO 92/14455 | 9/1992 |
| WO | WO 92/18496 | 10/1992 |
| WO | WO 94/20085 | 9/1994 |
| WO | WO 95/04533 | 2/1995 |

OTHER PUBLICATIONS

Gutman et al. Anticancer Research, 1996, 16:3673-3678).*
Thomas et al. Current Opinion in Oncology, 2000, 12:564-573.*
Stewart et al., Clin. Cancer Res., 2004, vol. 10, No. 24, pp. 8170-8176.*
Cronstein, B.N. Inflammation, 1992, vol. 16, No. 5, pp. 411-423.*
Tribalto et al. Leukemia Res., 1985, vol. 9, No. 8, pp. 1043-1049 (Abstract Attached).*
Algire, "Vascular reactions of normal and malignant tissues in vivo. I. Vascular reactions of mice to wounds and to normal and neoplastic transplants," J. Natl. Cancer Inst. pp. 73-85 (1945).
Allegri, "Confermata l'inefficacia della talidomides nella terapia dei tumori," Gazzetta Medica Italiana pp. 124-127 (1964).
Ambs et al., "Interactive effects of nitric oxide and the p53 tumor suppressor gene in carcinogenesis and tumor progression," FASEB J. 11: 443-448 (1997).
Apt, "Effect of thalidmoide on the course of experimental Chagas' Disease," BOI. Chil. Parasitol. 20(3): 84-86 (1965).
Aronson et al., "Thalidomide-induced peripheral neuropathy. Effect of serum factor on nerve cultures," Arch. Dermatol. 120(11): 1466-147 (1984).
Bach et al., "Studies on the possible anti-neoplastic effect of thalidomide," ACTA PathologicaET Microbiologica Scandinavica 59-491-499 (1963).
Bach et al., "Thalidomide in cancer chemotherapy," Lancet 1: 1271 (1963).
Bahmer. "Therapie bel lymphozytischer infiltration," Der Hautarzt 43: 663 (1992).
Balabanova et al., "Lupus erythcrmatosus hypertrophicus et profundus," Z. Hautkr 67(9): 812-815 (1992).
Barnes. et al., "Tumor Necrosis Factor Production in Patients with Leprosy", Infection and Immunity. vol. 60 No. 4. pp. 1441-1446 (1992).
Barnhill. et al., "Thalidomide: Use and Possible Mode of Action in Reactional Lepromatous Leprosy and in Various other Conditions", J. Am. Acad. Dermatol., vol. 7, No. 3. pp. 317-323-(1982).

(Continued)

*Primary Examiner* — James Anderson
(74) *Attorney, Agent, or Firm* — Jones Day

(57) ABSTRACT

The present invention comprises a group of compounds that effectively inhibit angiogenesis. More specifically, thalidomide and various related compounds such as thalidomide precursors, analogs, metabolites and hydrolysis products have been shown to inhibit angiogenesis and to treat disease states resulting from angiogenesis. Additionally, antiinflammatory drugs, such as steroids and NSAIDs can inhibit angiogenesis dependent diseases either alone or in combination with thalidomide and related compounds. Importantly, these compounds can be administered orally.

10 Claims, 7 Drawing Sheets

OTHER PUBLICATIONS

Barnhill, R. et al., "Studies on the Anti-inflammatory Properties of Thalidomide: Effects on Polymorphonuclear Leukocytres and Monocytes". J. A& Acad. Derm., vol. 11, No. 5, Part 1, pp. 814-819 (1984).

Barriere. H., "Traitement par la thalidomide". La Presse Mkdicale, vol. 12. No. 15. pp. 963 (1983).

Bazzoli, et al., "The Effects of Thalidomide and Two Analogues on the Regenerating Forelimb of the Newt", J. Embryol. Exp. Morph., vol. 41, pp. 125-135 (1977).

Beck, Jr. et al. "Vascular Development: Cellular and Molecular Regulation", The FASEB Journal, vol. 11, pp. 365-374 (1997).

Beccerica, E., "L'approccio terapeutico al paziente anziano con artrite reumatoide", Clin. Ter., vol. 122, pp. 289-298 (1987).

Belaube, P. et al., "Should Thalidomide be Rehabilitated?", Sem. Hop. Paris, vol. 59, No. 45, pp. 3101-3104 (1983).

Bensinger, W.I., "Supportive Care in Marrow Transplantation", Curr. Opin. Oncol., vol. 4, No. 4, pp. 614-623 (1992).

Bernal, et al., "Cellular Immune Effects of Thalidomide in Actinic Prurigo", Int'l. J, of Dermat., vol. 31, No. 8, pp. 599-600 (1992).

Blair, R. et al., "Human Mast Cells Stimulate Vascular Tube Formation", Journal of Clinical Investigation, vol. 99, No. 11, pp. 2691-2700 (1997).

Blaschke, V. et al., Chromatographische Racernattrennung von Thalidomid and teratogene Wirkung der Enantiomere, Arzneimittel Forsch./Dru,q Res., vol. 29, No. 11, pp. 1640-1642 (1979).

Bonifacino, J. et al., "A Peptide Sequence Confers Retention and Rapid Degradation in the Endoplasmic Reticulum", Science, vol. 2, pp. 79-80 (1990).

Bonnetblanc, et al., "Thalidomide and Recurrent Aphthous Stomatitis: a Follow-up Study", Dermatology, vol. 193, No. 4, pp. 321-323 (1996).

Boodman, S.G., "Questions About a Popular Prenatal Test", The Washington Post (1992).

Bowers, et al., "Effect of Thalidomide on Orogenital Ulceration", Br. Med. Journ., vol. 287, No. 6395, pp. 799-800 (1983).

Braun et al., "Thalidomide metabolite inhibits tumor cell attachment to concanavalin a coated surfaces," Biochem. Biophys. Res. Comm. 98(4): 1029-1034 (1981).

Braun, A.G. et al., "Teratogen Metabolism," Energy Research Abstracts, U.S. Department of Energy, Technical Information Center Office of Scientific & Technical Information, 9(8):5508:15072 (1984).

Braun, A.G. et al., "Teratogen Metabolism: Activation of Thalidomide and Thalidomide Analogues to Products that Inhibit the Attachment of Cells to Concanavalin a Coated Plastic Surfaces," Energy Research Abstracts, U.S. Department of Energy, Technical Information Center Office of Scientific & Technical Information, 9(8):5508:15071 (1984).

Braun, A.G. et al., "Teratogen Metabolism : Activation of Thalidomide and Thalidomide Analogues to Products that Inhibit the Attachment of Cells to Concanavalin a Coated Plastic Surfaces," Biochemical Pharmacology 33(9):1471-1477 (1984).

Braun, A.G. et al., "Teratogen Metabolism : Activation of Thalidomide and Thalidomide Analogues to Products that Inhibit the Attachment of Cells to Concanavalin a Coated Plastic Surfaces," Revised Version, U.S. Department of Commerce, National Technical Information Services, Harvard Medical School: Boston, MA DE84006118 (1982).

Brem et al., "Interstitial chemotherapy with drug polymer implants for the treatment of recurrent gliomas," J. Neurosurg. 74: 441-446 (1991).

Bressler et al.. "Clinicopathologic Correlation of occult choroidal neovascularization in age-related mascular degeneration," Arch. Opthamol. 110: 827 (1992).

Brodthagen, "Significant response of oral aphthosis to thalidomide treatment." J. Am. Acad. Dermaol. 13(3): 509 (1985).

Brovarone et al., "Occhio e gravidanza." Minerva Ginecol 43: 141-167 (1991).

Browne et al., "Expression of recombinant human plasminogen and aglycoplasminogen in HeLa cells," Fibrinolysis 5: 257-260 (1991).

Bubl et al., "Dysphagia in dermatologic disease," Dysphagia 8(2): 85-90 (1993).

Buckley et al., "Pyoderma gangrenosum with severe pharyngeal ulceration," J. Royal Soc. Med. 83: 590-591 (1990).

Buelens, Treatment of a greade II astrocytoma with thalidomide (Phthalylglutamic acid imide) [Behandlung eines astrocytoms II. Grades mit thaliomid (N-Phthalyglutaminsaureimid)], Arzneim-Forsch., 17(5): 646-648 (1967).

Bullock, "The clinical significance of erythema nodosum," Hosp. Pract. 21(3):102E-2H, 102K-2L, 102Q-2R pas (1986).

Burger et al., "Epidermolysis bullosa acquisita a rare late complication of allogeneic bone marrow transplantation?" Bone Marrow transplantation 9(2): 139-141 (1992).

Burrows, "Thalidomide Modifies disease," Brit. Med. J. 307(6909): 939-940 (1993).

Buckley et al., "Pyoderma gangrenosum with severe pharyngeal ulceration," J. Royal Soc. Med. 83: 590-591 (1990).

Calnan et al., "Actinic prurigo (Hutchinson's Summer Prurugo)," Clin. Exp. Dermatol. 2(4): 365-372 (1977).

Cant, J.S., "Minor Ocular Abnormalities Associated With Thalidomide", The Lancet, p. 1134 (1966).

Carmichael, et al., "Thalidomide: A Restricted Role", Lancet, vol. 339, No. 8805, p. 1362 (1992).

Cashin, C.H. et al., "Angiogenesis and Chronic Inflammation", Agents and Actions, vol. 34, No. 314, pp. 332-338 (1991).

Casini, G. et al., "Preparazione Di Uno Degli Antipodi Ottici Della 2-Ftalimmidoglutarimmide", II Pharmaco, Ed. Sc., vol. XIX, F&C. 6, pp. 563-565 (1964).

Chapon, et al., "Neuropathies Caused by Thalidomide", Rev. Neurol., vol. 141, No. 11, pp. 719-728 (1985).

Chaudhrv. A. et al.. "Effects of Prednisolone and Thalidomide on Induced Submandibular Gland tumors in Hampsters", Canc. Res., vol. 26, No. 9, Part 1, pp. 1884-1886 (1966).

Chen. T. et al., "Plasma Pharmacokinetics and Urinary Excretion of Thalidomide after Oral Dosing in Healthy Male Volunteers," The Am. Society for Pharma. andkxPeri. Therapeutics, vol. 17, No. 4, pp. 402-405 (1988).

Chosidow. O, et al.. "Sclerodermatous Chronic Graft-Versus-Host Disease: Analysis of Sevencases", J. Am. Acad. Dermatol., vol. 26. No. 1, pp. 49-55 (1992).

Claydon, et al., "Gastrointestinal Emergencies in HIV Infection", Balliere's Clin Gastroennterol., vol. 5, No. 4, pp. 887-911 (1991).

Clemmensen et al., "Thalidomide neurotoxicity," Arch. Dermatol. 120(3): 338-341 (1984).

Colville-Nash et al., "Angiogenesis and rheumatoid arthritis: Pathogenic and therapeutic implications," Ann. Rheum. Dis. 51: 919-625 (1992).

Congy, et al., "Plasma Zinc Levels in Elderly Patients Hospitalized in Long Stay Units. Correlations with Other Nutritional Markers. Immunological Tests and Survival", Sem. Hop. Paris, vol. 59. No. 45. pp. 3105-3108 (1983).

Costa, et al., "Aseptic Adenitis in a Patient with Pyoderma Gangrenosum", Ann. Dennatol., vol. 121, No. 8. pp. 550-552 (1994) (Abstract Only).

Crain, E. et al., "The Effect of Thalidomide on Experimental Autoimmune Myasthenia Gravis", J. of Autoimmunity, vol. 2, pp. 197-202 (1989).

Crawford, C.L.. "Letter: Thalidomide in Erythema Nodosum Leprosum", Lancet. vol. 2, No. 839. pp. 1201-1202 (1973).

Crawford, C.L.. "Treatment of Erythema Nodosum Leprosum with Thalidomide," Lancet, vol. 2, No. 828. pp. 567-568 (1973).

Crawford, C.L., "Use of Thalidomide in Leprosy [letter; comment]", BMJ, vol. 302, No. 6729. pp. 1603-1604 (1991).

Crum et al., 1985, "A new class of steroids inhibits angiogenesis in the presence of heparin or a heparin fragment," Science 230: 1375-1378 (1985).

Current Bibliographies in Medicine, "Thalidomide: Potential Benefits and Risks", National Inst. Health, National Library of Medicine pp. 1-72 (Jan. 1963-Jul. 1997).

Dark, et al., "Combretastin A-4, an Agent that Displays Potent and Selective Toxicity Toward Tumor Vasculature", Cancer Research, vol. 37, pp. 1829-1834 (1997).

David-Bajar, K.M., "Subacute Cutaneous Lupus Erythcmatosus", J. Invent. Dermatol. vol. 100. No. 1, pp. 2s-8s (1993).

D'Amato, R. J. et al., "Thalidomide is an Inhibitor of Angiogenesis", Proc. Natl. Acad. Sci., vol. 91, pp. 4082-4085 (1994).

D'Amato, et al., "Angiogenesis Inhibition in Age-Related Macular Degeneration", Opthalmology, vol. 102, No. 9, pp. 1261-1262(1995).

D'Amato. et al., "Microscopic Analysis of Retinal-Vessels Utilizing: Fluorescein-Labeled High-Molecular-Weight Dextrans," Invest. Opthamol. & Visual Science 33(4):1082 (1992).

De et al., "Possible antoneoplastic agents 1." J. Pharma. Sci. 64 (2) :262-266 (1975).

DeCock, "Treatment of Ulcerative Colitis," Brit. Med. J. 1: 1356 (1979).

DeKlerk et al., "New methods of treatment for renal allotransplants using the baboon as a primate experimental model," J. Urol. 102(5): 532-540 (1969).

Dhodapkar et al., "A phase II pilot study of anti-angiogenesis therapy using thalidomide in patients with multiple myeloma," UARK 98-003, pp. 1-15 (1995).

Dicken, C. H., "Malignant pyoderma", J. of the Am. Acad. of Dermatol., vol. 13, No. 6. pp. 1021-1025 (1985).

DiPaolo, et al., "Thalidomide: Effects on Ehrlich Ascites Tumor Cells in vitro". Science, vol. 144, pp. 1583 (1964).

DiPaolo, "Effect of thalidomide on a variety of transplantable tumors," Cancer Chemo. Reports, 22: 99-102 (1963).

DiPaolo, "In vitro test systems for cancer chemotherapy. II. Correlation of in vitroinhibition of dehydrogenase and growth with in vivo inhibition of Ehrlich ascites tumor," P.S.E.B.M. 114: 384-387 (1963).

DiPaolo et al., "Teratogenesis-oncogenesis: A study of possible relationships," Arch. Pathol. 81: 3-23 (1966).

Dorveaux et al., "Le traitement actuell du lupus crythemateux chronique," Le Concours Med. 106(31): 2957-2961 (1984).

Doutre et al., "Pyoderma gangrenosum and hemopathies. A propos of 2 cases," Nouv. Rev. Fr. Hematol. 29(4): 251-254 (1987).

Dunn, et al., "Bone Marrow Transplantation and Cataract Development", Arch. Ophthalmol. vol. 11 1, No. 10, pp. 1367-1373 (1993).

(Editorial) "Thalidomide in Dermatology and Leprosy". Lancet, vol. 2, No. 8446, pp. 80-81 (1985).

(Editorial) "Thalidomide Tested for Treatment of AIDS", U.S. Pharrn., vol. 18, No. 8, p. 14 (1993).

Eger, K. et al., "Synthesis, Central Nervous System Activity and Teratogenicity of a Homothalidomide." Arzheim. Forsch/Drug Res. 40(II)(10): 1073-1075 (1990).

Ehrlich, "Behcet's Disease: Current Concepts," Comprehensive Therapy 15(1): 27-30 (1989).

Elia et al., "Giant esophageal ulcer treated with steroids in AIDS patient(2)," J. Acquired Immune Defic. Syndr. 5(8):848-849 (1992).

Eisenbud. L. et al.. "Recurrent Aphthous Stomatitis of the Behcet's Type: Successful Treatment with FA Thalidomide", Oral Surgery, oral Medicine. Oral Pathology, vol. 64; No. 3, pp. 289-292 (1987).

Eravelly. J. et al., "Thalidornide in Weber-Christian Disease", The Lancet, vol. 1, No. 8005, p. 251 (1977).

Eriksson, et al., "Drug Exposure and Flow Cytometry Anaylses in a Thalidomide Treatment Schedule that Prolongs Rat Cardiac Graft Survival", Transplant Proc., vol. 24, No. 6, pp. 2560-2561 (1992).

Eriksson, S. O. et al., "Synthesis and Alkaline Hydrolysis of Some N-substituted Phthalimides", Acta Pharm. Suecica 10:63-84 (1973).

Fabro, S. et al.. "The Metabolism of Thalidomide: Some Biological Effects of Thalidomide and its Metabolites", Brit. J. Pharmacol., vol. 25, pp. 350-362 (1965).

Fabro, S. et al., "Teratogenic Activity of Thalidomide and Related Compounds", Life Sci., vol. 3, pp. 987-992 (1964).

Fabro, S. M.D., "Biochemical Basis of Thalidomide Teratogenicity", The Biochemical Basis of Chemical Teratogenesis, Chapter 5, pp. 159-178 (1981).

Fajardo, et al., "Dual Role of Tumor Necrosis Factor-a in Angiogenesis", Am. J. Pathol., vol. 140, No. 3, pp. 539-544 (1992).

Faure, et al., "PMN Leukocytes Chemotaxis: Inhibition by Thalidomide", Pathol. Biol. (Paris), vol. 29, No. 10, pp. 601-604 (1981).

Faure, et al., "Inhibition of PMN Leukocytes Chemotaxis by Thalidomide", Arch. Dermatol. Res., vol. 269, No. 3, pp. 275-280 (1980).

Fazal, N. et al., "Effect of Blocking TNF-a on Intracellular BCG (Bacillus Calmette Guerin) Growth in Human Monocyte-Derived-acrophages", FEMS Microbiology Immunology, vol. 105, pp. 337-346 (1992).

Fickentschcr, K. et al., "Stereochemical Properties and Teratogenic Activity of Some Tetrahydrophthalimides" Mol. Pharmacol., vol. 13, pp. 133-141 (1977).

Field, E. O. et al., "Effect of Thalidomide on Splenomegaly (GVH Reaction) in the Chick Embryo. Treatment of Donor Cells Only", Nature, vol. 211, No. 5055, pp. 13b9-1310 (1966).

Flohe, L. et al., "Studies on the Hypothetical Relationship of Thalidomide-induced Embryopathy and Collagen Biosynthesis", Arzneimitte/Forschung (Germany west). vol. 31, No. 2. pp. 315-320 (1981).

Folkman et al., "Angiogenesis," J. Biol. Chem. 267(16): 10931-10934 (1992).

Folkman et al., "Angiogenesis inhibition and tumor regression caused by heparin or a heparin fragment in the presence of cortisone," Science 221:719-725 (1983).

Folkman, J. et al., "Induction of Angiogenesis During the Transition from Hyperplasia to Neoplasia", Nature vol. 339, pp. 58-61 (1989).

Folkman J. et al., "Tumor Behavior in Isolated Perfused Organs: In Vitro Growth and Metastases of Biopsy material in Rabbit Thyroid and Canine Intestinal Segment", Anals of Surgery, pp. 491-502 (1966).

Folkman, J., "Tumor Angiogenesis: Therapeutic Implications", The New England J. of Med., vol. 285, No. 21, pp. 1182-1186. (1971).

Folkman, J., "Angiogenesis and Its Inhibitors", Important Advances in Oncology. J.B. Lippincott H. Company, pp. 42-62 (1985).

Folkman. J., "Angiogenesis in Cancer, Vascular, Rheumatoid and Other Disease", Nature Medicine. vol. 1, No. 1 pp. 27-30 (1995).

Folkman, J.. What is the Evidence that Tumors are Angiogenesis Dependent?, J. Naat' Cancer Inst., vol. 82 No. 1 (1990).

Francois, J., "Embryological Pigment Eputhelial Dystrophies", Opthalmologica. vol. 172, pp. 417-433 (1976).

Fuller, et al., "Thalidomide, Peripheral Neuropathy and AIDS". Int. J. STD AIDS, vol. 2, No. 5. pp. 369-370 (1991).

Furner,, B.B., "Treatment of Subacute Cutaneous Lupus Erythematosus". Int. J. Demzatol., vol. 29. No. 8, pp. 542-547 (1990).

Gad et al., "Thalidomide Induces Imbalances in T-Lymphocyte Sub-Populations in the Circulating Blood of Healthy Males", Lepr. Rev., vol. 56, No. 1, pp. 35-39 (1985).

Gaetani, "Studi Sull Attivita antitumorale della talidomide," Giornale Italiano diu Chemioterapia pp. 83-86 (1994).

Gehanno et al., "Mouth and pharyngeal hyperalgesic syndromes in AIDS," Ann. Otolaryngol. Chir. Cervicofac 107(5): 311-313 (1990).

Genvo et al., "Treatment of aphthosis with thalidomide and with colchicine," Dermatologica 168(4): 182-188 (1984).

Geoghiou et al., "HIV-assoc oesophageal ulcers treated with thalidomide," Med. J. Australia 152: 382-383 (1990).

Gershbein, "Effect of transplantedtumor and various agents on liver regeneration during pregnancy," P.S.E.B.M. 126: 88-92 (1967).

Gershbein, "The thalidomide analog, EM 12, enhances 1,2-dimethylhydrazine-induction of rat colon adenocarcinomas," Cancer Lett. 60: 129-133 (1991).

Gershbein, "Effect of various agents of liver regeneration and walker tumor growth in partially hepactectomized rats." Cancer Res. 26(9): 1905-1908 (1996).

Ghigliotti et al., "Thalidomide: Treatment of choice for aphthous ulcers in patients seropositive for human immunodeficiency virus," J. Am. Acad. Dermaol. 28(2 Part I): 271-272 (1993).

Gimbrone et al., "Tumor dormancy in vivo by prevention of neovascularization," J. Exp. Med. 136: 261-276 (1972).

Gimbrone et al., 1974, "Tumor growth and neovascularization: An experimental model using the rabbit cornea," J. Nat. Cancer Institute 52(2): 13-419 (1974).

Goihman-Yahr et al., "Significance of neutrophil activation in reactional lepromatous leprosy: Effects of thalidomide in vivo and in vitro. Activation in adjuvant disease," Int. Arch. Allergy Appl. Immun. 57: 317-332 (1978).

Goihman-Yahr et al., "Autoimmune diseases and thalidomide II: Adjuvant disease, experimental allergic encephalomyelitis and experimental allergic neuritis of the rat," Int. J. Leprosy 42(3): 266-275 (1974).

Gordon, G. "Mutagenic and Cytotoxic Studies with Thalidomide," (unpublished Ph.D. dissertation, The John Hopkins U.) (microformed on UMI Dissertation Abstracts database 8120023) (1981).

Gordon, G.B. et al., "Thalidomide Teratogenesis: Evidence for a Toxic Arene Oxide Metabolite," Federation of American Societies for Experimental Biology Federation Proceedings, 40(3): 2508 (1981).

Gordon. G.B. et al., "Thalidomide Teratogenesis: Evidence for a Toxic Arene Oxide Metabolite," Proc. Natl. Acad. Sci., 78(4): 2545-2548 (1981).

Gorin et al., "Thalidomide may cure AIDS ulcers," Nurs, Times 86(24): 10 (1990).

Gorin et al., "Thalidomide in hyperalgic pharyngeal ulceration of AIDS," Lancet 335: 1343 (1990).

Goulden et al.. "Linear prurigo simulating dermatitis artefacta in dominant dystrophicepidermolysis bullosa." Br. J. Dermatol. 129(4): 443-446 (1993).

Grabstald et al., "Clinical experiences with thalidomide in patients with cancer," Clin. Pharmacol. and Ther. 6: 298-302 (1965).

Grant et al.. "Scatter factor induces blood vessel formation in vivo," PNAS 90: 1937-1941 (1993).

Grinspan et al., "Treatment of aphthae with thalidomide." J. Am. Acad. Dermatol. 20(6): 1060-1063 (1989).

Grinspan, "Significant response of oral aphthosis to thalidomide treatment," Am. Acad. of Dermatol. 12(I, Part 1): 85-90 (1985).

Grosshans et al.. "Thalidomide therapy for inflammatory dermatoses." Int. J. Dermatol. 23(9): 598-602 (1984).

Guidetti et al., "Riccrche Sull'azione immunodepressiva della talidomide e del prednisolone in ratti portatori di neoplasie sperimentalmente indotte," Cancro 22: 503-512 (1969).

Gunzler, "Thalidomide in human immunodeficiency virus (HIV) patients. A review of safety considerations," Drug Saf. 7(2): 116-134 (1992).

Gunzler, "Thalidomide—A therapy for the immunological consequences of HIV infection?" Medical Hypothesis 30(2): 105-109 (1989).

Gutierrez-Rodriguez et al., "Treatment of refractory rheumatoid arthritis—The thalidomide experience," J. Rheumatol. 16(2): 158-163 (1989).

Gutierrez-Rodriguez et al., "Thalidomide: A promising new treatment for rheumatoid arthritis," Arthritis and Rheumatism 27(10): 1118-1121 (1984).

Haffner, "Studies involving orphan products for treating/diagnosing women's diseases," Food and Drug Law J. 48: 205-211 (1992).

Hamza, "Behcet's Disease, pamlmoplantar pustulosis and HLA-B27 treatment with thalidomide," Clin. Exp. Rheumatol. 8(4): 427 (1990).

Hamza, "Treatment of Behcet's disease with thalidomide," Clin. Rheumatol. 5(3): 365-371 (1986).

Handley et al., "Chronic bullous disease of childhood and ulcerative colitis," Pediatric Dermatol. 10(3): 256-258 (1986).

Handley et al., "Chronic bullous disease of childhood and ulcerative colitis," Brit. J. Dermatol. 127(Supp. 40): 67-68 (1992).

Harindra et al., "Papulo-pruritic eruption and giant ulceration of the mouth: A difficult clinical feature to treat in the patient infected with human immunodeficiency virus(I)," Arch. Intern. Med. 152(9): 1924 (1992).

Harris, "Antiangiogenesis for cancer therapy," Lancet 349(Supp. II): 13-15 (1997).

Hasper, "Chronic cutaneous lupus erythematosus. Thalidomide treatment of 11 patients," Arch. Dermatol. 19(10): 812-815 (1983).

Haver et al., "Thalidomide in the treatment of chronic discoid lupus," Acta. Derm. Venereol. 62(4): 321-324 (1982).

Hastings et al., "Thalidomide in the treatment of erythema nodosum leprosum. With a note on selected laboratory abnormalities nodosum leprosum," Clin. Pharmacol. Ther. 11(4): 481-487 (1970).

Hatfill et al., "Induction of morphological differentiation in the human leukemic cell line K562 by exposure to thalidomide metabolites," Leuk. Res. 15(2/3): 129-136 (1991).

Hayashi et al., "A synthetic peptide for a chemokines inhibits the growth of melanoma cell lines," J. Clin. Invest. 99(11): 2581-2587 (1997).

Heaton et al., "Graft-versus-host disease following liver transplantation," J.R. Soc. Med, 85(6): 313-314 (1992).

Hellman et al., "Prolongation of skin homograft survival by thalidomide," Brit. Med. J. 2: 687-689 (1965).

Helm et al.. "Comparative teratological investigation of compounds structurally and pharmacologically related to thalidomide." Arzneim. Forsch./Drug Res. 31(1, No. 6): 941-949 (1981).

Hendler et al., "Thalidomide for autoimmune disease," Medical Hypotheses 10: 437-443 (1983).

Hendler. "Immune modulators thalidomide," The Oxygen Breakthrough, William Morrow & Co.., $1^{st}$ Ed. pp. 217-219 (1989).

Heney et al., "Thalidomide treatment for chronic graft-versus-host disease," Brit. J. Haematol. 78: 23-27 (1991).

Heney et al., "Thalidomide in the treatment of graft-versus-host disease," Biomed. Pharmacother. 44(4): 199-204 (1990).

Heney et al., "Thalidomide for chronic graft-versus-host disease in children." Lancet 2(8623): 1317 (1988).

Hojyo et al., "Actinic prurigo (9)," Int. J. Dermatol. 31(5): 372-373 (1992).

Holm et al., "Chronic cutaneous lupus erythematosus treated with thalidomide," Arch. Dermatol. 129(12): 1548-1550 (1993).

Hori et al., "Suppression of solid tumor growth by immunoneutralizing monoclonal antibody against human basic fibroblast growth factor," Cancer Res. 51: 6180-6184 (1991).

Hu, "Inhibition of angiogenesis in rats by IL-1 receptor antagonist and selected cytokine antibodies," Inflammation 18: 45-58 (1994).

Hu et al., "A novel regulatory function of protcoltically cleaved VEGF-2 for vascular endothelial and smooth muscle cells," FASEB J. 11: 498-504 (1997).

Ingber et al., "Synthetic analogues of fumagillin that inhibit angiogenesis and suppress tumor growth," Lett. to Nature 348: 555-557 (1990).

Ingber, "Drug news and trial developments," AIDS Patient Care 6(6): 288 (1990).

Jacobson et al., "Thalidomide for the treatment of oral aphthous ulcers in patients with human immunodeficiency virus infection," New Engl. J. Med. 336(21): 1487-1493 (1997).

Jacobson et al., "The Diagnosis and treatment of leprosy," South Med. J. 69(8): 979-985 (1976).

Jager et al., "Clinical observations in the treatment of leprosy reaction with cyclic imides," Int. J. Lepr. Other Mycobact. Dis. 39(2): 589 (1971).

Jeltsch et al., "Hypeplasia of lymphatic vessels in VEGF-C transgeneic mice," Science 276: 1423-1426 (1997).

Jenkins et al., "Thalidomide, orogenital ulcers, and risk of teratogenicity," Lancet 1(8417-8418): 511 (1985).

Jennings et al., "Effect of actinomycin D on the production of acute phase protein in the rabbit," Experienta 25: 305-306 (1969).

Jew et al., "Thalidomide in erythema nodosum leprosum." DICP 24(5): 482-483 (1990).

Johnke et al., "Thalidomide treatment of prurigo nodularis," Ugeskr Laeger 155(38):3028-3030, Abstract (1993).

Jonsson, "Chemical structure and teratogenic properties IV. An outline of a chemical hypothesis for the teratogenic action of thalidomide." Acia Pharm. Siccica 9: 543-562 (1972).

Jonsson, "Chemical structure and teratogenic properties I. Synthesis and teratogenic activity in rabbits of some derivatives of phthalimide, isoindoine-1-one, 1.2-benzisothiazoline-3-one-1. 1-dioxide and 4(3II)-quinazoline." Acia Pharm. Succica, 9: 431-436 (1972).

Jonsson, "Chemical structure and teratogenic properties III. A review of available data on structure-activity relationships and mechanism of action of thalidomide analogues," Acia Pharm. Succia 9: 521-542 (1972).

Jorizzo et al.. "Thalidomide effects of behcet's syndrome and pustular vasculitis." Arch. Intern. Med. 146(5): 878-881 (1986).

Juret et al., "Absebce d'effet carcino-frenateur du talidomide vis-á-vis de deux tumerus greffees," Societe de Biologie 23: 246-249 (1963).

Kaitin, "Graft-versus-host disease," N. Engl. J. Med. 325(5): 357-358 (1991).

Kaplan et al.. "TNFα regulation of HIV 1:Biology and therapy," Res. In Immunol. 145(8-9): 685-690 (1994).

Katsuta et al., "Carcinogenesis in tissue culture. 3. Effects of the second treatments on DAB-Induced proliferating liver cells of normal rats in culture." Jpn. J. Exp. Med. 35(4): 231-248 (1965).

Keenan et al.. "Irnmunosuppresive properties of thalidomide," Transplantation 52(5): 908-910 (1991).

Kenyon et al., "The Discovery of New Inhibitors of Angiogenesis Using an Improved Mouse Corneal Neovascularization Model", Association for Research in Vision and Opthalmology, 1995 Annual Meeting, Fort Lauderdale, Florida, No. 459-367, p. S94 (Abstract Only) (1995).

Kim et al., "Inhibition of vascular endothelial growth factor-induced angiogenesis suppresses tumor growth in vivo," Lett. to Nature 362: 841-844 (1993).

Kitamoto et al., "Vascualr endothelial growth factor in an essential molecule for mouse kidney development: Glomerulogenesis and nephrogenesis," J. Clin. Invest. 99(10): 2351-2357 (1997).

Klug et al., "Embryotoxic effects of thalidomide derivatives in the non-human primate *Callithrix jacchus*," Arch. Toxicol. 68: 203-205 (1994).

Knighton et al., "Avascular and vascular phases of tumor growth in the chick embryo," Br. J. Cancer 35: 347-356 (1977).

Knop et al., "Thalidomide in the treatment of sixty cases of chronic discoid lupus erythematosus," Br. J. Dermatol. 108(4): 461-466 (1983).

Koch et al., "4 thalidomide and congeners as anti-inflammatory agents," Progress in Medical Chem. 22: 166-242 (1985).

Korn et al., "The second international workshop on scleroderma research," Matrix 13(5): 427-429 (1993).

Kroger et al., "Synergistic effects of thalidomide and poly (ADP-ribose) polymerase inhibition on type II collagen-induced arthritis in mice," Inflammation 20(2): 203-215 (1996).

Kundu et al., "*Prurigo nodularis* in an HIV positive man (2)," Genitourinary Med. 71(2): 129-130 (1995).

Kurkcuoglu et al., "Thalidomide in the treatment of recurrent necrotic mucocutaneous aphthae," Br. J. Dermatol. 112(5): 632 (1985).

Lane et al., "Treatment of actinic prurigo with intermittent short-course topical 0.05% clobetasol 17-propionate: A preliminary report," Arch. Dermatol, 126(9): 1211-1213 (1990).

Languillon, "The effects of thalidomide on leprosy reaction," Int. J. Lepr. Other Mycobact. Dis. 39(2): 590-592 (1971).

Larsson, "Treatment of severe colitis in behcet's syndrome with thalidomide (CG-217)," J. of Intern. Med. 228: 405-407 (1990).

Ledo. "Photodermatosis, Part I: Photobiology, photoimmunology, and idiopathicphotodermatoses," Int. J. Dermatol. 32(6): 387-396 (1993).

Lehner et al., "Thalidomide, orogenital ulcers, and the risk of teratogenesis," Lancet 8423: 288-289 (1985).

Lenicque, "Action of thalidomide on the induction of tentacles in regenerating hydra littoralis," Acta. Zool. 127-139 (1967).

Levy et al., "Treatment of erythema nodosum leprosum with thalidomide," Lancet 2(824): 324-325 (1973).

Lien et al., "The blood supply of experimental liver metastases. II. A tnicrocurculatory study of the normal and tumor vessels of the liver with the use of perfused silicone rubber," Surgery 68(2): 334-340 (1970).

Lisek, C.A. "Structural Elucidation of a Hydroxylated Metabolite of Thalidomide: Evidence Supporting an Arene Oxide Intermediate," (unpublished Ph.D. dissertation. The John Hopkins U.) (microformed on UMI Dissertation Abstracts database 8609337) (1985).

Lo et al., "Treatment of discoid lupus erythematosus." Int. J. Dermatol. 28(8): 497-507 (1989).

Londono, "Thalidomide in the treatment of actinic prurigo," Int. J. Dermaol. 12(5): 326-328 (1973).

Lovell et al., "Thalidomide in actinic prurigo," Br. J. Dermatol. 108(4): 467-471 (1983).

Lopez et al.. "Thalidomide as therapy for intestinal chronic GVHD," Bone Marrow Transplant. 11(3): 251-252 (1993).

Louzir et al., "Erythroleucemie chez un patient avant une maladie de behcet et traite au long cours par thalidomide," Ann. de Med. Interne 143: 479-480 (1992).

Lueprasitsakul et al.. "Effect of thalidomide on the incidence of iodine-induced and spontaneous lymphocytic thyroiditis and spontaneous diabetes mellitus in the BB/Wor rat," Acta Endocrino Logica 123: 79-83 (1990).

Luers, "Failure of mutagenic action of thalidomide in Drosphila," Lancet II(7258): 1332 (1962).

Magana-Garcia, "Antimalarials for children," J. Am. Acad. Dermatol. 30(3): 510 (1994).

Malone et al.. "Inhibition of angiogenesis by recombinant human platelet factor-4 and related peptides," Science 2: 77-78 (1990).

Makonkawkeyoon et al., "Thalidomide inhibits the replication of human immunodeficiency virus type 1," PNAS 90: 5974-5978 (1993).

Marin-Padilla et al., "Thalidomide induced alterations in the blastocyst and placenta of the armadillo, dasypus novemcinctus Mexicanus, including a choriocarcinoma," Am. J. Pathol. 43(6): 999-1016 (1963).

Mascaro et al., "Thalidomide in the tratment of recurrent, necrotic, and giant mucocutaneous aphthae and aphthosis," Arch. Dermt. 115: 636-637 (1979).

Matsubara et al., "Inhibition of human endothelial cell proliferation by gold compounds," J. Clin. Invest. 79: 1440-1446 (1987).

Matsuyama et al., "Cytokines and HIV infection: in AIDS a tumor necrosis factor disease?" AIDS 5(12): 1405-1417 (1991).

Mauad, "Melhoras clinicas obtidas em doentes cancerous a avancados com tratamento pela talidomida associada a hormonios." Anais Paulistas Medicina e Cirurgia pp. 15-39 (1963).

Maurice et al., "The effect of thalidomide on arachidonic acid metabolism in human polymorphonuclear leukocytes and platelets," Br. J. Dermatol. 115(6): 677-680 (1986).

McCarthy et al., "Thalidomide for the therapy of graft-versus-host disease following allogenic bone marrow transplantation," Biomed. Pharmacother. 43(9): 693-697 (1989).

McKenna et al., "Linear IgA disease, oral ulceration and Crohn's disease," Br. J. Dermatol. 127: 67-68 (1992).

Meza et al., "Managing the gastrointestinal complications of AIDS," Drug Therapy 23(1 1): 74-83 (1993).

Miller et al., "Zusatnmentreffen einer thalidomid-induzierten fehlbildung mit einem malignen lymphom hohen malignitatsgrades." Monatsschr. Kinderheilkd. 128: 27-29 (1980).

Miller et al., "Treatment of chronic erythema nodosum leprosum with cyclosporine A produces clinical and immunohistologic remission." Int. J. Lepr. Other Mycobact. Dis. 55(3): 441-449 (1987).

Misery et al., "Remission of Langerhans cell histiocytosis with thalidomide treatment." Cli. Exp. Dermatol. 18(5): 487 (1993).

Miura et al., "Potentiating effect of thalidomide on methylcholanthrene oncogenesis in mice," Experientia 26(Fasc. 3): 305-306 (1970).

Miyachi. "A possible mechanism of actions of thalidomide on rheumatoid arthritis," Arthritis Rheumatol. 28(7): 836 (1985).

Miyachi et al., "Effects of thalidomide on the generation of oxygen intermediates by Zymosan-stimulated normal polymorphonuclear leukocytes," Arch. Dermatol. Res. 274(3-4): 363-367 (1982).

Mohri et al.. "Negative effect of thalidomide and relative substances on the growth of HeLa cells," Chem. Pharm. Bull. 16: 2289-2292 (1968).

Moncada et al.. "Thalidomide-effect on T Cell subsets as a possible mechanism of action," Int. J. Lepr. Other Mycobact. Dis. 53(2): 201-205 (1985).

Montrucchio et al., "Tumor necrosis factor a-induced angiogenesis depends on in situ platelet-acting factor biosynthesis." J. Exp. Med. 180: 377-382 (1994).

Moulin et al., "Treatment of Jessnet-Kanof disease with thalidomide," Ann. Dermatol. Venereol. 10(8): 611-614 (1983).

Mshana et al., "Thymus-dependent lymphocytes in leprosy II. Effect of chemotherapy on T-lymphocyte subpopulations," J. Clin. Immunol. 2(2): 69-74 (1982).

Muckter et al., "Thalidomide and tumor," Antimicrobial Agents and Chemother. pp. 531-538 (1965).

Mummery et al.. "Screening for cytotoxicity in neuroblastoma cells-I. Dependence of growth inhibition of the presence of serum," Toxicity Lett. 18: 201-209 (1983).
Munro et al., "Pyoderma gangrenosum associated with Behcet's syndrome-response to thalidomide," Clin. Exp. Dermatol. 13(6): 408-410 (1988).
Muthukkaruppan et al., "Angiogenesis in the mouse cornea," Science 205(28): 1416-1418 (1979).
Naafs et al., "Thalidomide therapy an open trial," Inlt. J. Dermatol, 24(2): 131-134 (1985).
Naafs, "Bangkok workshop on leprosy research. Treatment of reactions and nerve damage," Int. J. Lepr. Other Mycobact. Dis. 64(4, Supp.): S21-28 (1996).
Neubert, "Teratogenicity: Any relationship to carcinogenicity?" Instit. Toxicity Embryopharmacol., Free Univ. Berlin, Berlin, Federal Rep. of Germany, pp. 169-178 (1979).
Nguyen et al., "Elevated levels of the angiogenic peptide basic fibroblast growth factor in urine of bladder cancer patients," J. Natl. Cancer Inst. 85(3): 241-242 (1993).
Nguyen et al., "Elevated levels of the antiogenetic peptide basic fibroblast growth factor in urine of patients with a wide spectrum of cancers," J. Natl. Cancer Inst. 86(5): 356-361 (1994).
Nicolas et al., "Interferon alpha therapy in severe unresponsive subacute cutaneous lupus erythematosus," New Engl. J. Med. 321(22): 1550-1551 (1989).
Nicolau et al., "Thalidomide: Treatment of severe recurrent aphthous stomatitis in patients with AIDS," DICP 24(11): 1054-1056 (1990).
Nielson et al., , "Thalidomide nehances superoxide anion release from human polymorphonuclear and leukocytes," Acta. Pathol. Microbiol. Immunol. Scand. [C], 94(6): 233-237 (1986).
Obeso et al., "Methods in laboratory investigation: A hemangioendothelioma-derived cell line: Its use as a model for the study of endothelial cell biology," Lab. Invest. 63(2): 259-269 (1990).
Oikawa et al., "Eponemycin, a novel antibiotic is a highly powerful angiogenesis inhibitor," Biochem. Biophys. Res. Comm. 181(3): 1070-1077 (1991).
Olson et al., "Thalidomide (N-phthaloylglutamimide) in the treatment of advanced cancer," Clin. Pharmacol. Ther. 6(3): 292-297 (1965).
Orzalesi, "Il Danno iatrogeno in neonatologica," Ped. Med. Chir. 14: 105-112 (1992).
Ostraat et al., "Thalidomdie prolongs graft survival in rat cardiac transplants," Transplant. Proc. 24(6): 2624-2625 (1992).
Otsuka et al., "A new potent angiogenesis inhibitor, FR-118487," J. Microbiol. Biotechnol. 1(3): 163-168 (1991).
Paller et al., "Proceedings of the concurrent sesisons," Pediatr. Dermatol. 9(4): 397-406 (1992).
Passaniti et al., "Method in laboratory investigation: A simple. quantitative method for assessing angiogenesis and antiangiogenic agents using reconstituted basement membrane, heparin, and fibroblast growth factor," Lab, Invest. 67(4): 519-528 (1992).
Patey et al.. "Thalidomide et colite ulcereuse dans la maladie de Behcet."Gastronenterol. Clin. Biol. 13: 104-110 (1989).
Pearson et al.. "Treatment of moderately severe erythema nodosum leprosum with thalidomide—A double-blind controlled trial," Lepr. Rev. 40(2): 111-116 (1969).
Peyron et al., "The pharmacological basis for the treatment of photodermatoses," Biochimie 68(6): 899-904 (1986).
Pfordte, "Uber die beeinflussung des serumproperdinsystems durch verschiedene arzneimittel," Pharmazie 26: 301-302 (1971).
Phillips et al., , "Tumor necrosis factor alpha (rhTNF) fails to stimulate angiogenesis in the tabbit cornea," Anatomical Rec. 245: 53-56 (1996).
Powell et al., "Investigation and treatment of orogenital ulceration; studies on a possible mode of action of thalidomide," Brit. J. Dermatol. 113(Supp. 28): 141-144 (1985).
Prigent et al., "Sarcoidose cutanee traitement par la thalidomide," La Presse Medicale 12(47): 3007 (1983).
Proenca, "Thalidomide: An eclectic medication in dermatology," Rev. Paul. Med. 107(1): 41-46 (Abstract) (1989).
Radeff et al., "Recurrent aphthous ulcer in patient infected with human immunodeficiency virus: Successful treatment with thalidomide," J. Am. Acad. Dermatol. 23 (3, pt. 1): 523-525 (1990).

Rainsford, "Disease-modifying anti-rheumatic and immunoregulatory agents," Bailliere's Clin. Rheumatol. 4(3): 405-432 (1990).
Rajan et al., "A clinical study of thalidomide comparing pre-treatment and post-treatment reactional episodes and corticosteroid requirements," Lepr. India 55(1): 111-116 (1983).
Randall, "Investigational new drug (US) 'orphans' trials now use thalidomide from two source," JAMA 263(11): 1474 (1990).
Randall, "Thalidomide's back in the news, but in more favorable circumstances," JAMA 263(11): 1467-1468 (1990).
Revuz, "Actuante du thalidomide," Ann. Dermatol. Venereol. 117: 313-321 (1990).
Revuz et al., "Crossover study of thalidomide vs. placebo in severe recurrent aphthous stomatitis," Arch. Dermatol. 126: 923-927 (1990).
Rhoton, "Role for thalidomide in primary biliary cirrhosis treatment?" Gastroenterol. 105(3): 956 (1993).
Robbins, "The plasminogen-plasmin enzyme system," Fibrinolysis pp. 340-357 (1987).
Roe, "Pathology thalidomide and neoplasia," Nature 200: 1016-1017 (1963).
Roe at al.. "Tumour-incidence in progeny of thalidomide-treated mice," Brit. J. Cancer pp. 331-333 (1965).
Ruggenini et al., "Talidomide e tumori sperimentali," Cancro 20: 39-55 (1967).
Rustin et al., "Pyoderma gangrenosum associated with Behcet's disease: Treatment with thalidomide," J. Am. Acad. Dermatol. 23(5, pt. 1): 941-944 (1990).
Ryan et al., "Thalidomide to treat esophageal ulcer in AIDS (6)," New Engl. J. Med. 327(3): 208-209 (1992).
Salven et al., "Serum vascular endothelial growth factor is often elevated in disseminated cancer." Clin. Cancer Res. 3: 647-651 (1997).
Sampaio et al.. "Prolonged treatment with recombinant interferon gamma induces erythema nodosum lepromatous leprosy patients," J. Exp. Med. 175(6): 1729-1737 (1992).
Sampaio et al.. "Thalidomide selectively inhibits tumor necrosis factor alpha production by stimulated human monocytes." J. Exp. Med. 173(3): 699-703 (1991).
Santis, "Aphthous stomatitis and its management," Curr. Opin. Dent. 1(6): 763-768 (Abstract) (1991).
Santos et al., "In vitro tumor necrosis factor production by mononuclear cells from lepromatous leprosy patients and from patients with erythema nodosumleprosum." Clin. Immunol. Immunopathol. 67(3): 199-203 (1993).
Sato et al., "Increased concentration of vascular endothelial growth factor/vascular permeability factor in cyst fluid of enlarging and recurrent thyroid nodules," J. Clin. Endocrinol. Metabol. 82(6): 1968-1972 (1997).
Schweigerer et al., "Angiogenesis and andiogenesis inhibitors in paediatric diseases," European J. Peddiatr. 151: 472-476 (1992).
Shannon et al., "Inhibition of de nova IgM antibody synthesis by thalidomide as a relevant mechanism of action in leprosy," Scand. J. Immunol. 13(6): 553-562 (1981).
Shannon et al., "Thalidomide's effectiveness in erythema nodosum leprosum is associated with a decrease in CD4+ cells in the peripheral blood," Lapr. Rev. 63(1): 5-11 (1992).
Shealy et al., "D- and L-Thalidomide," Chem. and Indust. pp. 1030-1031 (1965).
Sheehan, "Thalidomide neurotoxicity and rheumatoid arthritis," Arthritis and Rheum. 29(10): 1296 (1986).
Sherman et al., "Thalidomide: A twenty-five year perspective," Food Drug Cosmetic Law J. 41: 458-466 (1986).
Sheskin, "The treatment of lepra reaction in lepromatous leprosy. Fifteen years' experience with thalidomide," Int. J. Dennatol. 19(6): 318-322 (1980).
Sheskin et al., "In vivo measurements of iron, copper, and zinc in the skin of prurigo nadularis patients treated with thalidomide," Dermatologica 162(2): 86-90 (1981).
Shi et al "Kringle domains and plasmin denaturation," Biochem. Biophys. Res. Comm. 178(1): 360-368 (1991).
Sidky et al., "Inhibition of angiogenesis by interferons: Effect on tumor and lymphocyte-induced vascular responses," Cancer Res. 47: 5155-5161 (1987).

Silverman, "Medical inflation," Persp. Biol. Med. pp. 617-637 (1980).
Smith et al., "Studies on the relationship between the chemical structure and embryotoxic activity of thalidomide and related compunds," Chem. Struct. and Embryopathy, Boston, Little Browne, pp. 194-209 (1965).
Srivastava et al., "The prognostic significance of tumor vascularity in intermediate-thickness skin melanoma," Am. J. Pathol. 133: 419-423 (Abstract from Medline Accession No. 06745734) (1988).
Style, "Early diagnosis and treatment of leprosy in the United States," Am. Family Phys. 52(1): 172-178 (1995).
Sugiura et al., "Effect of thalidomide on transplantable mouse, rat, and hampster tumors," Gann 55: 57-60 (1964).
Swift, "Thalidomide in erythema nodosum leprosum," Lancet 2(835): 966 (1973).
Szydlowska et al., "On the application of thalidomide as a block of functional groups of proteins in histochemical investigations," Folia Histo. Cytochem. 16(3): 233-240 (1978).
Tamura et al., "Combination thalidomide and cyclosporine for cardiac allograft rejection. Comparison with combination methylprodnisolone and cyclosporine," Transplantation 49(1): 20-25 (1990).
Tanaka et al., "Vascular endothelial growth factor in diabetic retinopathy," Lancet 349: 1520 (1997).
Taylor et al., "Protamine is an inhibitor of angiogenesis," Nature 297: 307-312 (1982).
Teppo et al., "Thalidomide-type malformations and subsequent osteosarcoma," Lancet 11(8034): 405 (1977).
"Thalidomide 20 years on," Lancet II(8245): 510-511 (1981).
"Thalidomide." March Index, 11th ed., pp. 1458 (1989).
Theophilus, "Treatment with thalidomide in steroid dependency and neuritis," Lepr. India 52(3): 423-428 (1980).
Thomas et al, "Effect of thalidomide on liver regeneration in rat," Indian J. Exp. Biol. 10: 314-315 (1972).
Thomas et al., 1972, "Lack of thalidomide induced aplasia in regenerating tail of lizard. hemidactylus tlavivirdis," Indian J. Exp. Biol. 10: 316-317 (1972).
Thomas et al., "Successful treatment of adult's langerhans cell histiocytosis with thalidomide," Arch. Dermatol. 129: 1261-1264 (1993).
Torry et al., "Angiogenesis in the uterus: Potential regulation and relation to tumor angiogenesis," Am. J. Reproductive Immunol, 27: 171-179 (1992).
Traldi et al.. "L'impiego dell'imide dell'acido n'ftalilglutammico (Talidomide) nella terapia sintomatica del vomito di molti pazienti affeti da neoplasia naligne o causato dalla somministrazione di cloridato di mecloretamina," Cancro 18: 336-341 (1965).
Trautman, "Treatment of Hansen's Disease," Cutis 18(1): 62-65 (1976).
Van den Broek, "Treatment of prurigo nodularis with thalidomide," Arch. Dermatol. 116(5): 571-572 (1980).
Vasilescu et al., "Cercetari privind actiunea talidomide asupra celulelor cultivate in vitro," Cerc. Fiziol. 13(4): 293-300 (1968).
Verhaul et al., "Combination oral antiangiogenic therapy with thalidomide ans sulindac inhibits tumor growth in rabbits," Brit. J. Cancer 79(1): 114-118 (1999).
Vincente et al., "In vitro activity of thalidomide against mycobacterium avium complex," Arch. Internal Med. 153: 334 (1993).
Villa et al., "Antimytotic effect of thalidomide and its metabolites on the chick embryo blood cells," Haematol. Latina 6: 217-221 (1963).
Villa et al., "Cytological effects of thalidomide," Lancet pp. 725 (1963).
Vladutiu, "Another chance for thalidomide?" Lancet I(7444): 981-982 (1966).
Vogelsang et al., "Thalidomide for the treatment of chronic graft-versus-host disease," New Engle. J. Med. 326: 1055-1059 (1992).
Vogelsang et al., "Therapy of chronic graft-versus-host disease in a rat model," Blood 74(1): 507-511 (1989).
Vogelsang et al., "Thalidomide induction of bone marrow transplantation tolerance," Transplant. Proc. 19(1, Pt. 3): 2658-2661 (1987).

Vogelsang et al., "Treatment and prevention of acute graft-versus-host disease with thalidomide in a rat model," Transplantation 41(5): 644-647 (1986).
Vogt et al., "Inhibition of angiogenesis in Kaposi's sarcoma by Captopril," Lancet 349: 1148 (1997).
Waters et al., "Treatment of ulcerative colitis with thalidomide," Brit. Med. J. 1(6166): 792 (1979).
Waters, "Use of thalidomide in leprosy," BMJ 303(6800): 470 (1991).
Waters, "An internally-controlled double-blind trial of thalidomide in severe erythema nodosum leprosum." Lepro. Rev. 42(1): 26-42 (1971).
Weidner et al., "Tumor angiogenesis and metastasis-correlation in invasive breast carcinoma," The New Engl. J. Med. 324(1): 1-8 (1991).
Weidner et al., "Tumor angiogenesis correlates with metastasis in invasive prostate cancer." Am. J. Pathol. 143(2): 401-409 (1993).
Weidner et al., "Tumor angiogenesis: A new significant and independent prognostic indicator in early-stage breast carcinoma," J. Nat. Cancer Inst. 84(24): 1875-1887 (1992).
Weslowski et al., "Effect of light on a murine model of retinopathy of prematurity," Invest. Opthamol. & Visual Science 33(4): 1281 (Abstract) (1992).
White et al., "Treatment of pulmonary hemangiomatosis with recombinant interferon alpha-2a." New Engl. J. Med. 32(18): 1197-1200 (1989).
Williams, "Enantiomers in arthritic disorders," Pharmacol. & Therapeutics 46(2): 273-295 (1990).
Williams et al., "Thalidomide hypersensitivity in AIDS," Lancet 337: 436-437 (1991).
Winkelmann et al., "Thalidomide treatment of prurigo nodularis," Acta. Derm. Venereol. 64(5): 412-417 (1984).
Wood et al., "The potential use of thalidomide in the therapy of graft-versus-host disease—A review of clinical and laboratory information," Lcuk. Res. 14(5): 395-399 (1990).
Woodyatt, "Thalidomide," Lancet pp. 750 (1962).
Wulff et al., "Development of polyneuropathy during thalidomide therapy," Br. J. Dermatol. 112(4): 475-480 (1985).
Yazici et al., "Practical treatment recommendations for pharmacotherapy of Behcet's syndrome," Drugs 42(5): 796-804 (1991).
Yoshimura et al., "Cloning, sequencing, and expression of human macrophage stimulating protein (MSP, MSTI) confirms MSP as a member of the family of Kringle proteins and locates the MSP gene on chromosome 3," J. Biol. Chem. 268(21): 15461-15468 (1993).
Youle et al., "Treatment of resistant aphthous ulceration with thalidomide in patients positive for HIV antibody," BMJ 298(6671): 432 (1989).
Youle et at, "Thalidomide in hyperalgic pharyngeal ulceration of AIDS," Lancet 335(8705): 1591 (1990).
Yue et al., "2-Methoxyestradiol, an endogenous estrogen metabolite, induces apoptosis in endothelial cells and inhibits angiogenesis: Possible role for stress-activated protein kinase signaling pathway and Fas expression," Molecular Pharmacol. 51: 951-962 (1997).
Zinche et al., "Nitric oxide synthase lies downstream from vascular endothelial growth factor-induced but not basic fibroblast growth factor-induced angiogenesis," J. Clin. Invest. 99(11): 2625-2634 (1997).
Zwart, "Treatment of grade II astrocytoma with thalidomide," Arzneim. Forsch. 16(12): 1688-1689 (1966).
Ace Animals, Inc.. www.aceanimals.com/SpragueDawley.htm, 2004, pp. 1-3.
Alexanian, Raymond et al., "Thalidomide for Resistant and Relapsing Myeloma," *Seminars in Hematology*, 2000, 37(1)Supp 3:22-25.
Avalos-Diaz, et al., "Inhibitory Effect on Endocytosis in Polymorphonuclear Cells Caused by Thalidomide", Arch. Invest. Med., vol. 16, No. 2, pp. 139-143 (1985).
Balk, Young Gon et al., "Thalidomide Therapy on a Case of Prurigo Nodularis", Ann. Dermatol., vol. 5, No. 2, pp. 117-120 (1993).
Barlogie, et al., "Duration of Survival in Patients with Myeloma Treated with Thalidomide," The New England Journal of Medicine. Jul. 10, 2008, 210-212.

Barr Laboratories, Inc.'s Answer, Counterclaims and Demand for Jury Trial, *Celgene Corporation v. Barr Laboratories, Inc.*, Civil Action No. 07-286 (SDW)(MCA), Aug. 13, 2008.

Bell, et al., "Glucocorticoid repression and basal regulation of the epoxide hydrolase promoter," Arch Biochem Biophys., Jun. 1990, 279(2):363-9, Abstract.

Bertolini, F. et al.. "Thalidomide in multiple myeloma, myelodysplastic syndromes and histiocytosis. Analysis of clinical results and of surrogate angiogenesis markers," *Annals of Oncology*, 2001, 12:987-990.

Brennen, W. Nathaniel, et al., "Thalidomide and Analogues: Current Proposed Mechanisms and Therapeutic Usage." Clinical Prostate Cancer, Jun. 2004, 54-61.

Brent, R. and Holmes, L., "Clinical and Basic Science Lessons from the Thalidomide Tragedy: What Have We Learned About the Causes of Limb Defects?", *Teratology*, 1988, 38:241-251.

Bruno, et al., "New drugs for treatment of multiple myeloma," The Lancet Oncology, 2004, 5(7):430-442.

Cavenaugh, Jamie D., "Thalidomide in Multiple Myeloma: Current Status and Future Prospects," *British Journal of Haematology*, 2003, 120:18-26.

Cordingley, F. et al., "Tumour Necrosis Factor as an Autocrine Tumour Growth Factor for Chronic B-Cell Malignancies," *The Lancet*, Apr. 30, 1988, 969-971.

D'Amato, Robert et al., "Mechanism of Action of Thalidomide and 3-Aminothalidomide in Multiple Myeloma," *Seminars in Oncology*, 2001, 28(6): 597-601.

Damaj, G, et al., "Thalidomide therapy induces response in relapsed mantle cell lymphoma", Leukemia, 2003, 17:1914-1915.

De, A. and Pal, D., "Possible Antineoplastic Agents II," *Journal of Pharmaceutical Sciences*, 1977, 66(2):232-235.

De, A. and Pal, D., "Quantitative Structure-Activity Relationship (QSAR) and Rational Drug Design for Some Antineoplastic Thalidomide and Glutarimide Derivatives," *J. Indian Chem. Soc.*, 1976, LIII:1049-1052.

Dhodapkar, et al., "A Phase II Pilot Study of Anti-Angiogenesis Therapy Using Thalidomide in Patients with Multiple Myeloma", UARK 98-003, pp. 1-15 (1998).

Eleutherakis-Papaiakovou, et al., "Bone Marrow Angiogenesis and Progression in Multiple Myeloma: Clinical Significance and Therapeutic Approach," Leukemia and Lymphoma, 2003, 44(6):937-948.

Ferrari, et al., "Differential effects of human recombinant interleukin-1 beta and dexamethasone on hepatic drug-metabolizing enzymes in male and female rats," Biochem Pharmacol., Jun. 1993, 45(11):2269-77, Abstract.

Folkman, J. and Klagsburn, M., "A family of angiogenic peptides," *Nature*, 1987, 329:671-672.

Folkman, Judah, "Angiogenesis: an organizing principle for drug discovery?", Nature Reviews, Apr. 2007, 6:273-286.

Furman, R.R., "Thalidomide alone or in combination with fludarbabine are effective treatments for patients with fludarabine-relapsed and refractory CLL", American Society of Clinical Oncology, May 2005, Abstract #6640.

Furman, Richard, "Thalidomide With or Without Fludarabine in Treating Patients with Hematologic Cancer", ClinicalTrials.gov on Dec. 31, 2007.

Furman, Richard, et al., "Thalidomide is active alone and in combination with fludarabine in fludarabine-relapsed and refractory chronic lymphocytic leukemia". Dec. 2004, Abstract #4835.

Game, Melaka, et al.. "Thalidomide and low dose Vinblastine as palliative therapy for patients relapsing after autotransplant for Hodgkin's Disease (HD) and Non-Hodgkin's Lymphoma (NHL)", American Society of Hematology, Dec. 2001, Abstract #5235.

Genovesi, "Effects of the Administration of Thalidomide on Corneal Heterografts," *Ophtalmology Clinic of the University of Messina*, 13 pp., 1965.

Gilani, S., "Cardiovascular Malformations in the Chick Embryo Induced by Thalidomide," *Toxicology and Applied Pharmacology*, 1973, 25:77-83.

Goy, Andre, "New Directions in the Treatment of Mantle Cell Lymphoma: An Overview", Clinical Lymphoma & Myeloma, Oct. 2006, 7(Supp 1):S24-S32.

Hatjiharissi, et al., "The Combination of Intermediate Doses of Thalidomide and Dexamethasone Reduces Bone Marrow Micro-Vessel Density But Not Serum Levels of Angiogenic Cytokines in Patients with Refractory/Relapsed Multiple Myeloma," Hematological Oncology, 2004, 22(4):159-68.

Hershman et al., "Alpha$_2$ interferon in the prevention of N-nitrosomethyl urea induced breast cancer in rats," Eu. J Surgical Oncology, Jun. 1988, 14(3):249-251.

Iino et al., "Effects of OK-432 Picibanil on Estrogen Receptor Levels and Tamoxifen Treatment in 7,12-Dimethylbenz[a]anthracene-Induced Rat Mammary Cancers," Onocology, 1990, 47(2):185-190.

In Ethanol-Fed Rats, Biosis AN 1990:450534, Nutrition Res., 1990, 10(8):915-928, Abstract.

Johnson et al., "Relationships between drug activity in NCI preclinical in vitro and in vivo models and early clinical trials," British J. of Cancer, 2001, 84(10):1424-1431.

Juliusson, Gunnar et al., "Frequent good partial remissions from thalidomide including best response ever in patients with advanced refractory and relapsed myeloma," *British Journal of Haematology*, 2000, 109:89-96.

Jurand, A., "Early changes in limb buds of chick embryos after thalidomide treatment," J. Embryol. Exp. Morph., Oct. 1966, 16(2):289-300.

Kakimoto, T. et al., "Thalidomide for the Treatment of Refractory Multiple Myeloma: Association of Plasma Concentrations of Thalidomide and Angiogenic Growth Factors with Clinical Outcome," *Jpn. J. Cancer Res.*, 2002, 93:1029-1036.

Kantorowitz et al., "Effect of Conjoint Administration of Tamoxifen and High-Dose Radiation on the Development of Mammary Carcinoma," Medline AN 93246378, International J. Radiation Oncol., Biol., Physics, Apr. 30, 1993, 26(1):89-94, abstract.

Kerbel, et al., "Clinical Translation of Angiogenesis Inhibitors," Nature Reviews Cancer, 2002, 2:727-739.

Kim, et al., "In vivo radioprotective effects of oltipraz in gamma-irradiated mice," Biochem Pharmacol, May 1998, 55(10):1585-90, Abstract.

Kneller, A. et al., "Therapy with thalidomide in refractory multiple myeloma patients—the revival of an old drug," *British Journal of Haematology*, 2000, 108:391-393.

Kreuter, Michael, et al., "Downregulation of neuropilin-1 in patients with acute myeloid leukemia treated with thalidomide", European Journal of Haemotology, 2007. 79:392-397.

Kumar, et al., "Effect of thalidomide therapy on bone marrow angiogenesis in multiple myeloma," Leukemia, 2004, 1-4.

Kumar, S. et al., "Thalidomide as an anti-cancer agent," *J. Cell. Mol. Med.*, 2002, 6(2):160-174.

Lakartidningen, Fallbeskrivning, "Thalidomide—a possible alternative as an immune-modulating drug," *Lakartidningen*, 1989, 86(48):4260-4262.

Larson, Melissa, et al., "HIV-related Lymphoma Treated with Maintenance Thalidomide", Clinical Advances in Hematology & Oncology. Mar. 2005, 3(3):231-235.

Leibovich, S. et al.. "Macrophage-induced angiogenesis is mediated by tumour necrosis factor-α," Nature, 1978, 329:630-632.

Mauad MJ., Anais Paulistas de Medicina e Cirurgia. "Clinical Improvements Obtained in Advanced Cancer Patients with Treatment with Thalidomide Associated with Hormones". 86. pp. 13-40 (Jul. 1963).

Missirlis, E. et al., "Angiogenesis is Associated with Collagenous Protein Synthesis and Degradation in the Chick Chorioallantoic Membrane," *Tissue and Cell*, 1990, 22(4):419-426.

Nam, et al., "Correlation of increased mortality with the suppression of radiation-inducible microsomal epoxide hydrolase and glutathione S-transferase gene expression by dexamethasone: effects on vitamin C and E-induced radioprotection," Biochem-Pharmacol., Nov. 1998, 56(10):1295-304, Abstract.

Pagnini et al., Boll. Soc. Ital. Biol. Sperim., 39, pp. 1360-1363 (1963).

Peuckmann, Vera et al., "Potential Novel Uses of Thalidomide," *Drugs*, 2000, 60(2):273-292.

Rageh, M. et al., "Vasculture in Pre-Blastema and Nerve-Dependent Blastema Stages of Regenerating Forelimbs of the Adult Newt, Notophthalmus viridescens," *Journal of Experimental Zoology*, 2002, 292:255-266.

Raje, Noopur et al., "Thalidomide and immunology drugs as cancer therapy," *Current Opinions in Oncology*, 2002, 14:635-640.

Rajkumar, et al., "Thalidomide in the Treatment of Plasma Cell Malignancies," Journal of Clinical Oncology, 2001, 19(16):3593-3595.

Rajkumar, S. Vincent, "Thalidomide in Multiple Myeloma," Oncology, 2000, 14(12) Supplement 13:11-16.

Rajkumar, S.V. et al., "Thalidomide for previously untreated indolent or smoldering multiple myeloma," *Leukemia*, 2001, 15:1274-1276.

Rajkumar, S.V. et al., "Thalidomide in the Treatment of Relapsed Multiple Myeloma," *Mayo Clin Proc.*, 2000, 75:897-901.

Rajkumar, S.V., "Thalidomide in the treatment of multiple myeloma," *Expert Rev. Anticancer Ther.*, 2001, 1(1):20-28.

Ramasamy, Karthik, et al., "Successful treatment of refractory angioimmunoblastic T-cell lymphoma with thalidomide and dexamethasone", Haematologica, 2006, 91(1):117-118.

Ribatti, D. et al, "Is thalidomide a true anti-angiogenic molecule in multiple myeloma?" *Haematologica*, 2002, 87(4):344-345.

Ribatti, et al., "On the use of thalidomide as an antiangiogenic agent in the treatment of multiple myeloma," Ann. Hematol., 2003, 82:262.

Richardson, et al., "Thalidomide: Emerging Role in Cancer Medicine," Annu. Rev. Med., 2002, 53:629-657.

Rinaldi, "Thalidomide and Morphogenetic Processes in the Adult. Effect of Thalidomide on the Regeneration of the Tail Triturus Cristatus," Boll. Soc. Ital. Biol., 1969, 45(13):1268-1272.

Roe, F.J.C., "Research on Anticarcinogenic Effects of Thalidomide," *The Practitioner*, 1974, 212(1269):296-297.

Ruan, Jia, et al., "Targeting angiogenesis in mantle cell lymphoma: Clinical efficacy and correlative studies of a phase II trial of RT-PEPC (rituximab. thalidomide and metronomic oral chemotherapy with prednisone, etoposide, procarbazine and cyclophosphamide) in relapsed/refractory disease)", American Society of Hematology. Dec. 2006, Abstract #2751.

Sausville et al., "Contributions of human tumor xenografts to anti-cancer drug development," Cancer Research, 2006, 66:3351-3354.

Schulze-Osthoff, K. et al, "In Situ detection of basic fibroblast growth factor by highly specific antibodies," Am. J. Pathol. 1990, 137(1), pp. 85-92.

Simmons, et al., "Induction of the hepatic mixed-function oxidase system by synthetic glucocorticoids," The Journal of Biological Chemistry, 1987, 262(1):326-332.

Smith, A. and Wolpert, L., "Nerves and angiogenesis in amphibian limb regeneration," *Nature*, 1975, 257:224-225.

Steins, M.B., et al., "Thalidomide for the Treatment of Acute Myeloid Leukemia", Leukemia & Lymphoma, Sep. 2003, 44(9):1489-1493.

Steins, Martin, et al., "Efficacy and safety of thalidomide in patients with acute myeloid leukemia", Blood, Feb. 2002, 99(3):834-839.

Strupp, C., et al., "Hairy cell leukemia (HCL) with extensive myelofibrosis responds to thalidomide", Leukemia Research, 2005, 29:967-969.

Thomas, Deborah, et al., "Current role of thalidomide in cancer treatment," Current Opinion in Oncology, 2000, 12:564-573.

Thompson et al., "Effect of Dietary Iron Deficiency or Excess on the Induction of mammary Carcinogenesis by 1-Methyl-1-Nitrosourea," Medline AN 91105904, Carcinogenesis, Jan. 1991, 12(1):111-114.

Tosi, Patrizia et al, "Thalidomide in multiple myeloma: state of art" *Haematologica*, 2002, 87(3):233-234.

Tsutsumi, S. and Gidoh, M., "Inefficacy of Thalidomide on Rat Adjuvant-induced Arthritis and Lack of Arthrogenicity of Hansen Bacilli,"*Jap. J. Leprosy*, 1988, 57:122-128.

Vacca, A. et al., "Bone marrow angiogenesis and progression in multiple myeloma," *British Journal of Haematology*, 1994, 87:503-508.

Vacca, et al., "Thalidomide Down regulates Angiogenic Genes in Bone Marrow Endothelial Cells of Patients with Active Multiple Myeloma," Journal of Clinical Oncology, 2005, 23(23):5334-5346.

Wöhrer, Stefan, et al., "Effective treatment of primary plasma cell leukemia with thalidomide and dexamethasone—a case report", The Hematology Journal, 2004, 5:361-363.

Wolpert, L., "Mechanisms of Limb Development and Malformation," *Br. Med Bull.*, 1976, 32(1):65-70.

Zangari, et al., "Eight-year median survival in multiple myeloma after total therapy 2: roles of thalidomide and consolidation chemotherapy in the context of total therapy 1," British Journal of Haematology, 2008, 141:433-444.

Letter from Sterne, Kessler, Goldstein & Fox dated May 22, 2008 regarding Supplemental Notification Pursuant to § 505(j)(2)(B)(ii) of the Federal Food, Drug, and Cosmetic Asct.

Communication in corresponding Canadian Patent Application No. 2,514,681 dated Jan. 5, 2009.

Interlocutory Decision of Opposition to EP Patent No. 1 264 597 dated Nov. 9, 2009.

Korean Patent Infringement Decision in 506043 dated Dec. 21, 2009.

* cited by examiner

METHODS AND COMPOSITIONS FOR INHIBITION OF ANGIOGENESIS

RELATED APPLICATIONS

This application is a continuation of U.S. application Ser. No. 11/411,230, filed Apr. 26, 2006, now U.S. Pat. No. 7,435,745, which is continuation of U.S. application Ser. No. 09/287,377, filed Apr. 7, 1999, now abandoned, which is a continuation of U.S. application Ser. No. 08/963,058, filed Nov. 3, 1997, now abandoned, which claims priority to U.S. provisional application Ser. No. 60/028,708, filed Nov. 5, 1996, all of which are incorporated herein in their entireties by reference.

TECHNICAL FIELD

The present invention relates to methods and compositions for preventing unwanted angiogenesis in a human or animal. More particularly, the present invention relates to a method for preventing unwanted angiogenesis, particularly in angiogenesis dependent or associated diseases, by administration of compounds such as thalidomide and related compounds.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, Scleritis, Steven's-Johnson disease, radial keratotomy, pemphigoid and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or chorioiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing's sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-borne tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., *Nature* 297:307 (1982). The toxicity of protamine limits its practical use as a therapeutic. Folkman et al. have disclosed the use of heparin and steroids to control angiogenesis. See Folkman et al., *Science* 221:719 (1983) and U.S. Pat. Nos. 5,001,116 and 4,994,443. Steroids, such as tetrahydrocortisol, which lack gluco and mineral corticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon a or human interferon β has been shown to inhibit tumor-induced angiogenesis in mouse dermis stimulated by human neoplastic cells. Interferon β is also a potent inhibitor of angiogenesis induced by allogeneic spleen cells. See Sidky et al., *Cancer Research* 47:5155-5161 (1987). Human recombinant a interferon (alpha/A) was reported to be successfully used in the treatment of pulmonary hemangiomatosis, an angiogenesis-induced disease. See White et al., *New England J. Med.* 320:1197-1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1.

PCT Application No. WO 92/14455 to Kaplan et al. is directed to a method for controlling abnormal concentration of TNF-a by administering thalidomide or thalidomide derivatives to a patient with toxic concentrations of TNF-a.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage could be distributed in a form that the patient could self-administer.

SUMMARY OF THE INVENTION

In accordance with the present invention, compositions and methods are provided that are effective in inhibiting unwanted angiogenesis. These compositions are easily administered by different routes, including orally, and can be given in dosages that are safe and provide angiogenic inhibition at internal sites. The present invention provides a method of treating mammalian diseases mediated by undesired and uncontrolled angiogenesis by administering a composition comprising an anti-angiogenic compound in a dosage sufficient to inhibit angiogenesis.

The present invention also includes angiogenic inhibiting compounds that contain an epoxide group. These angiogenic inhibiting compounds can be administered to a human or animal alone or with epoxide hydrolase inhibiting compounds.

The present invention also includes compositions comprising an anti-angiogenesis compound and an antiinflammatory compound. The antiinflammatory compound can be either a steroidal or nonsteroidal antiinflammatory compound. Nonsteroidal antiinflammatory compounds, called NSAIDS, are preferred.

The present invention is especially useful for treating certain ocular neovascular diseases such as macular degeneration. The compounds which are contemplated as part of the present invention preferably can be given orally to the patient and thereby halt the progression of the disease. Other disease that can be treated using the present invention are diabetic retinopathy, neovascular glaucoma and retrolental fibroplasia.

Accordingly, it is an object of the present invention to provide a compound and method to inhibit unwanted angiogenesis in a human or animal.

It is yet another object of the present invention to provide a composition for inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases.

It is another object of the present invention to provide a method and composition for the treatment of diabetic retinopathy.

Another object of the present invention is to provide a method and composition comprising thalidomide and antiinflammatory drugs for the treatment of angiogenesis dependent diseases.

It is another object of the present invention is to provide a method and composition comprising thalidomide and steroidal antiinflammatory drugs for the treatment of angiogenesis dependent diseases.

It is yet another object of the present invention is to provide a method and composition comprising thalidomide and nonsteroidal, antiinflammatory drugs for the treatment of angiogenesis dependent diseases.

It is another object of the present invention is to provide a method and composition comprising angiogenesis inhibiting compounds and antiinflammatory drugs for the treatment of angiogenesis dependent diseases.

Yet another object of the present invention is to provide a method and composition comprising angiogenesis inhibiting compounds and steroidal antiinflammatory drugs for the treatment of angiogenesis dependent diseases.

Another object of the present invention is to provide a method and composition comprising angiogenesis inhibiting compounds and nonsteroidal antiinflammatory drugs for the treatment of angiogenesis dependent diseases.

It is an object of the present invention to provide a method and composition antiinflammatory drugs for the treatment of angiogenesis dependent diseases.

It is another object of the present invention to provide a method and composition comprising steroidal antiinflammatory drugs for the treatment of angiogenesis dependent diseases.

It is yet another object of the present invention to provide a method and composition comprising nonsteroidal antiinflammatory drugs for the treatment of angiogenesis dependent diseases.

Another object of the present invention is to provide a method and composition comprising thalidomide and antiinflammatory drugs for the treatment of cancer.

Yet another object of the present invention is to provide a method and composition comprising thalidomide and steroidal antiinflammatory drugs for the treatment of cancer.

Another object of the present invention is to provide a method and composition comprising thalidomide and nonsteroidal antiinflammatory drugs for the treatment of cancer.

It is an object of the present invention to provide a method and composition comprising antiinflammatory drugs for the treatment of cancer.

It is another object of the present invention to provide a method and composition comprising steroidal antiinflammatory drugs for the treatment of cancer.

It is yet another object of the present invention to provide a method and composition comprising nonsteroidal antiinflammatory drugs for the treatment of cancer.

These and other objects, features and advantages of the present invention will become apparent after a review of the following detailed description of the disclosed embodiments and the appended claims.

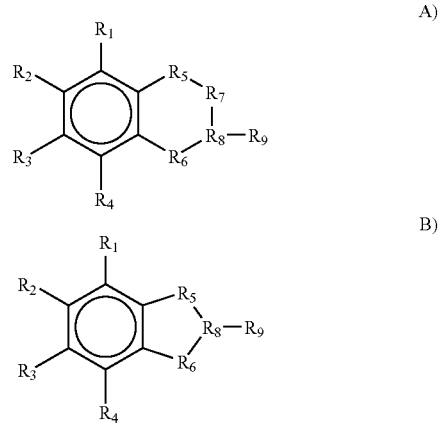

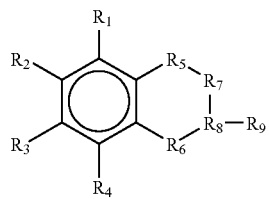

A)

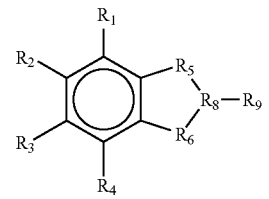

B)

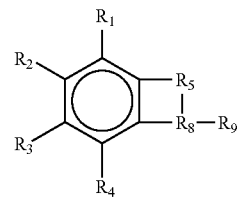

C)

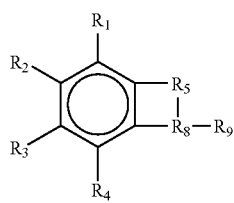

C)

Figure 4:
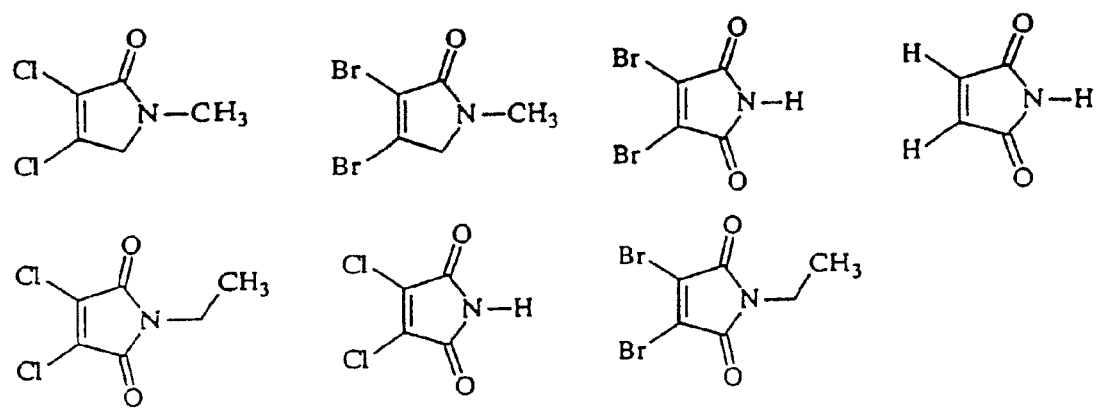

FIG. 4 is a listing of representative compounds in the genus represented by the following general formula:

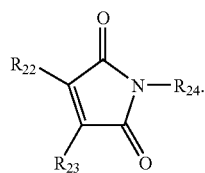

Figure 5:
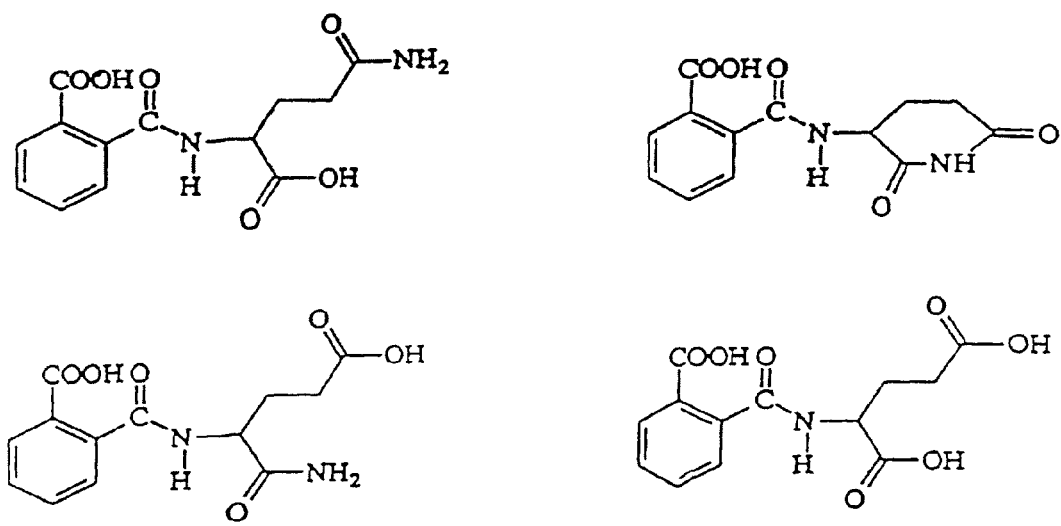

FIG. 5 is a listing of representative compounds in the genus represented by the following general formula:

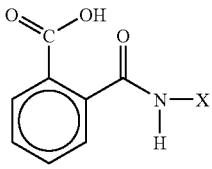

Figure 6:
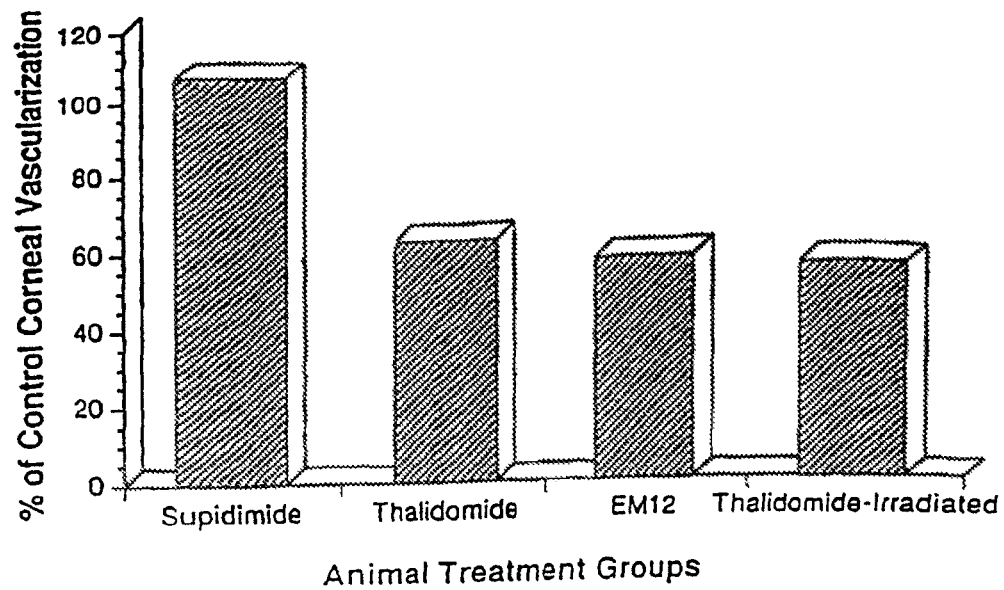

FIG. 6 shows the effect of thalidomide and EM12 on angiogenesis in a rabbit cornea model of angiogenesis.

Figure 7:
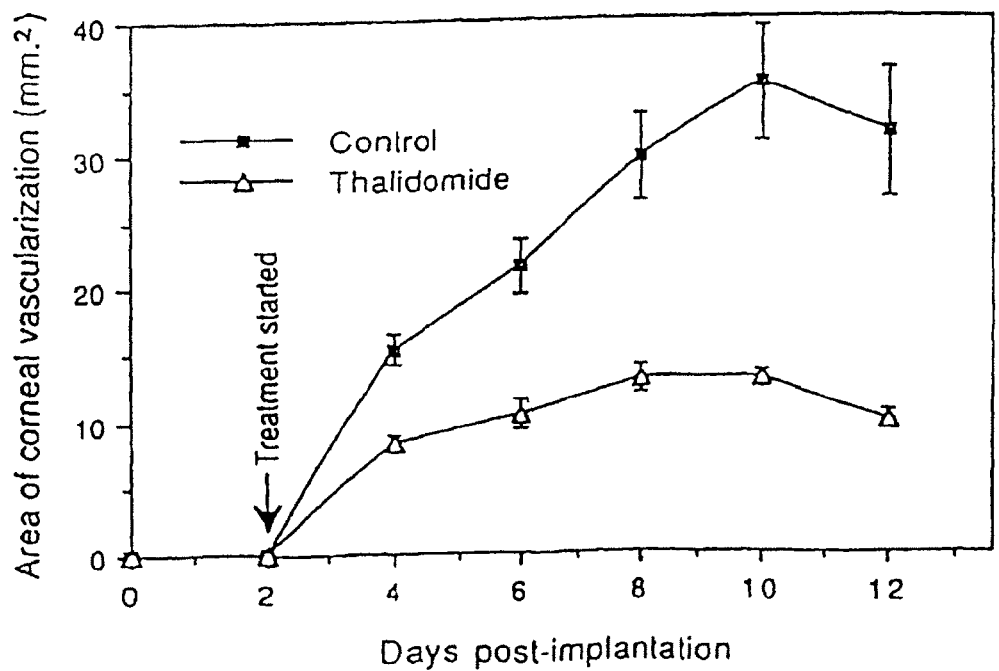

FIG. 7 shows the effect of thalidomide on the area of corneal vascularization in a rabbit cornea model of angiogenesis.

Figure 8:
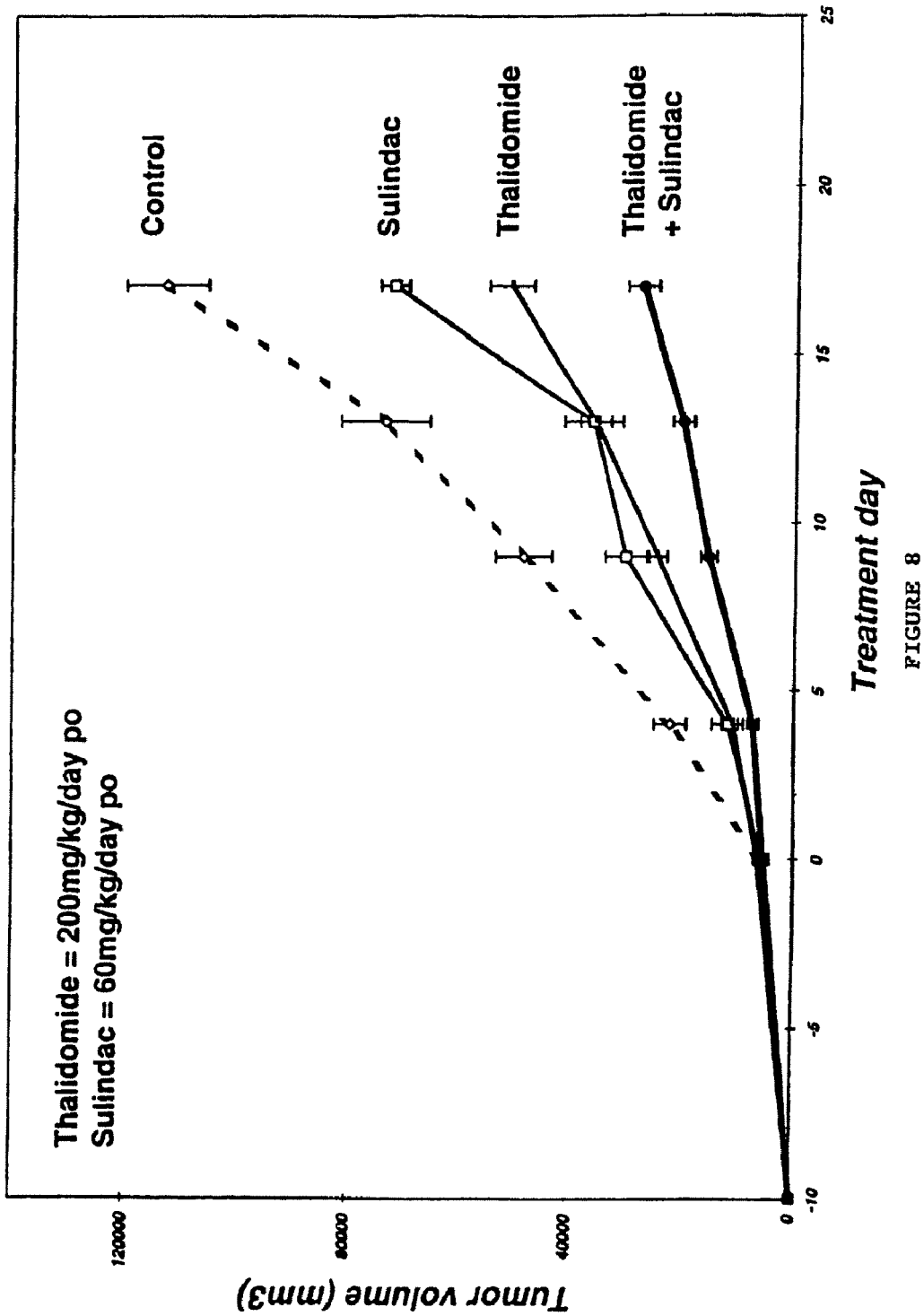

FIG. 8 shows the effect of thalidomide, sulindac, or a combination of the two on the inhibition of tumor growth of V2-carcinoma in New Zealand White female rabbits.

DETAILED DESCRIPTION

The present invention includes compositions and methods for the treatment of diseases that are mediated by angiogenesis. One embodiment of the present invention is the use of thalidomide or the metabolites of thalidomide as disclosed herein to inhibit unwanted angiogenesis. The present invention also includes compounds which cause dysmelia in the developing fetus and have anti-angiogenic activity. The present invention comprises a method of treating undesired angiogenesis in a human or animal comprising the steps of administering to the human or animal with the undesired angiogenesis a composition comprising an effective amount of a teratogenic compound that is anti-angiogenic.

Compounds that can be used in accordance with the present invention include compounds included in the following general formulae. Examples of compounds that have anti-angiogenic properties having one of the following three formulae (A), (B), or (C):

In the above formulae, A), B), and C), $R_1$, $R_2$, $R_3$ and $R_4$ can be selected from: —H; —OH; =O, straight and branched chain alkanes, alkenes, alkynes; cyclic alkanes, alkenes, and alkynes; combinations of cyclic and acyclic alkanes, alkenes, and alkynes; alcohol, aldehyde, ketone, carboxylic acids, esters, or ether moieties in combination with acyclic, cyclic, or combination acyclic/cyclic moieties; aza; amino; —$XO_n$, or —O—$XO_n$, where X=N and n=2; X=S and n=2 or 3; or X=P and n=1–3; and halogens; $R_5$, $R_6$, $R_7$, and $R_8$ are each independently selected from:

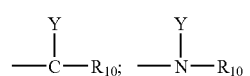

or —O— where Y is optional and is the same as defined above for $R_1$; and $R_{10}$ is the same as defined above for $R_1$, or when Y is absent, $R_{10}$ is =O; and $R_9$ is a moiety having formula D), E), F), G) or H):

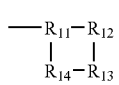

D)

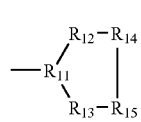

E)

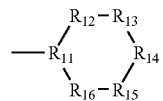

F)

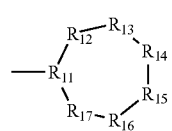
(G)

where each of $R_{11}$-$R_{17}$ is independently the same as defined above for $R_5$;

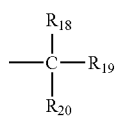
(H)

where $R_{18}$, $R_{19}$ and $R_{20}$ are, independently selected from

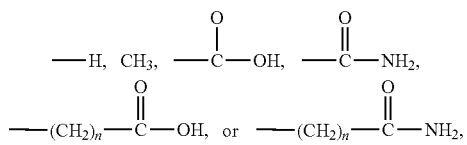

and n=1 to 4.

Accordingly, another aspect of the present invention features inhibiting angiogenesis in a mammal by administering a therapeutic composition comprising one of the above-described compounds in a dosage sufficient to inhibit angiogenesis.

Figure 1:
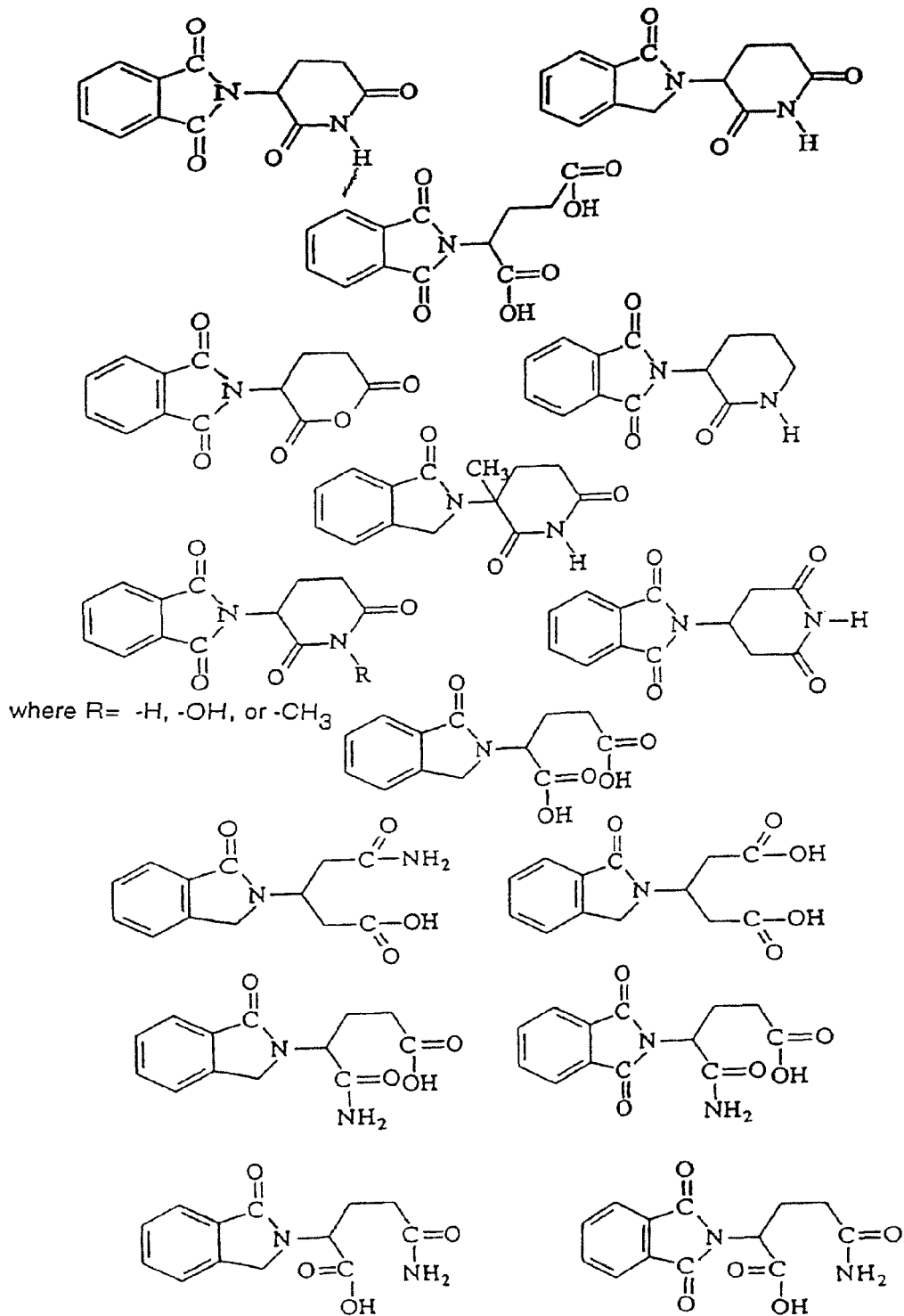
FIGS. 1 through 3 are a listing of representative compounds in the genus represented by the following general formulas.
Figure 2:
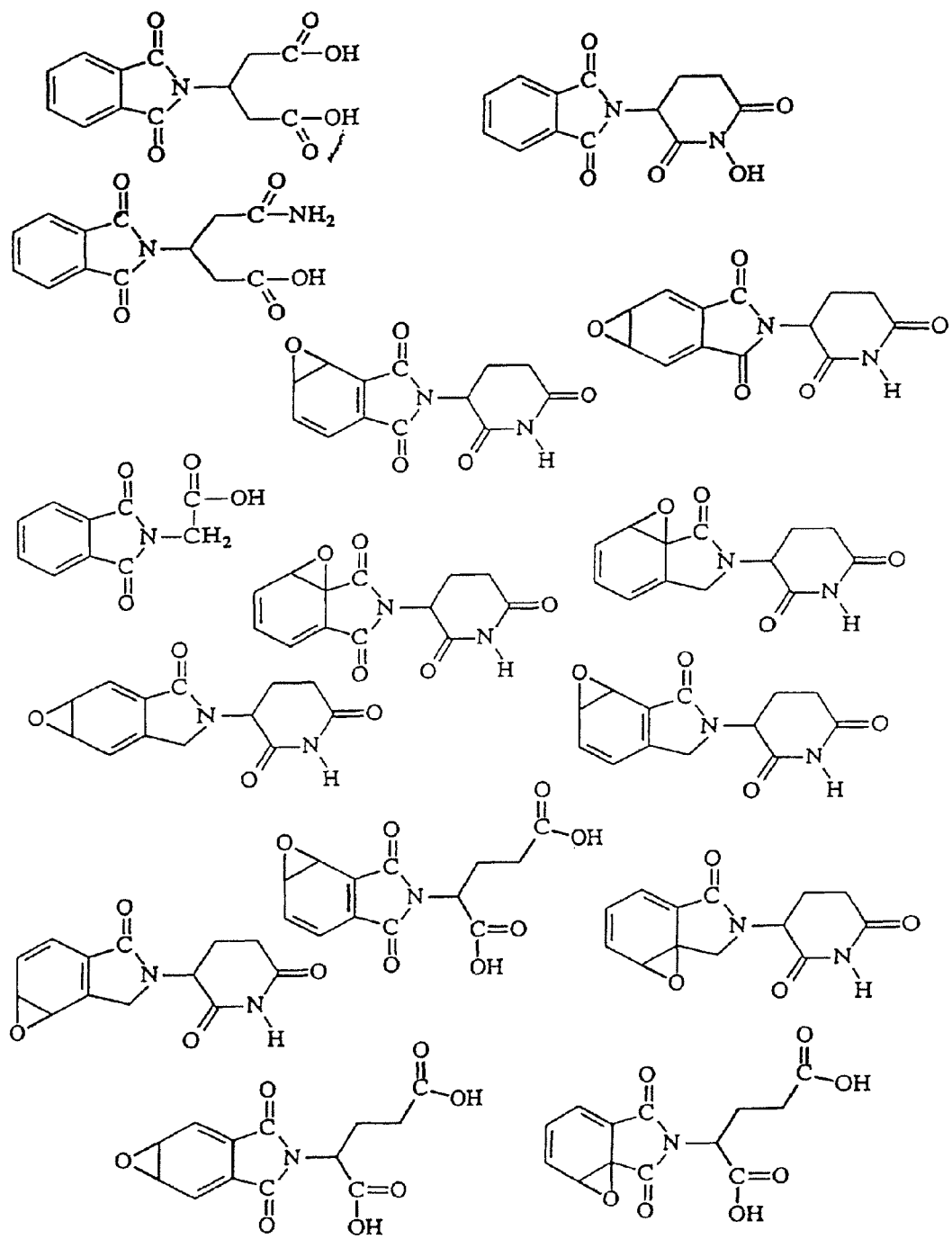
Figure 3:
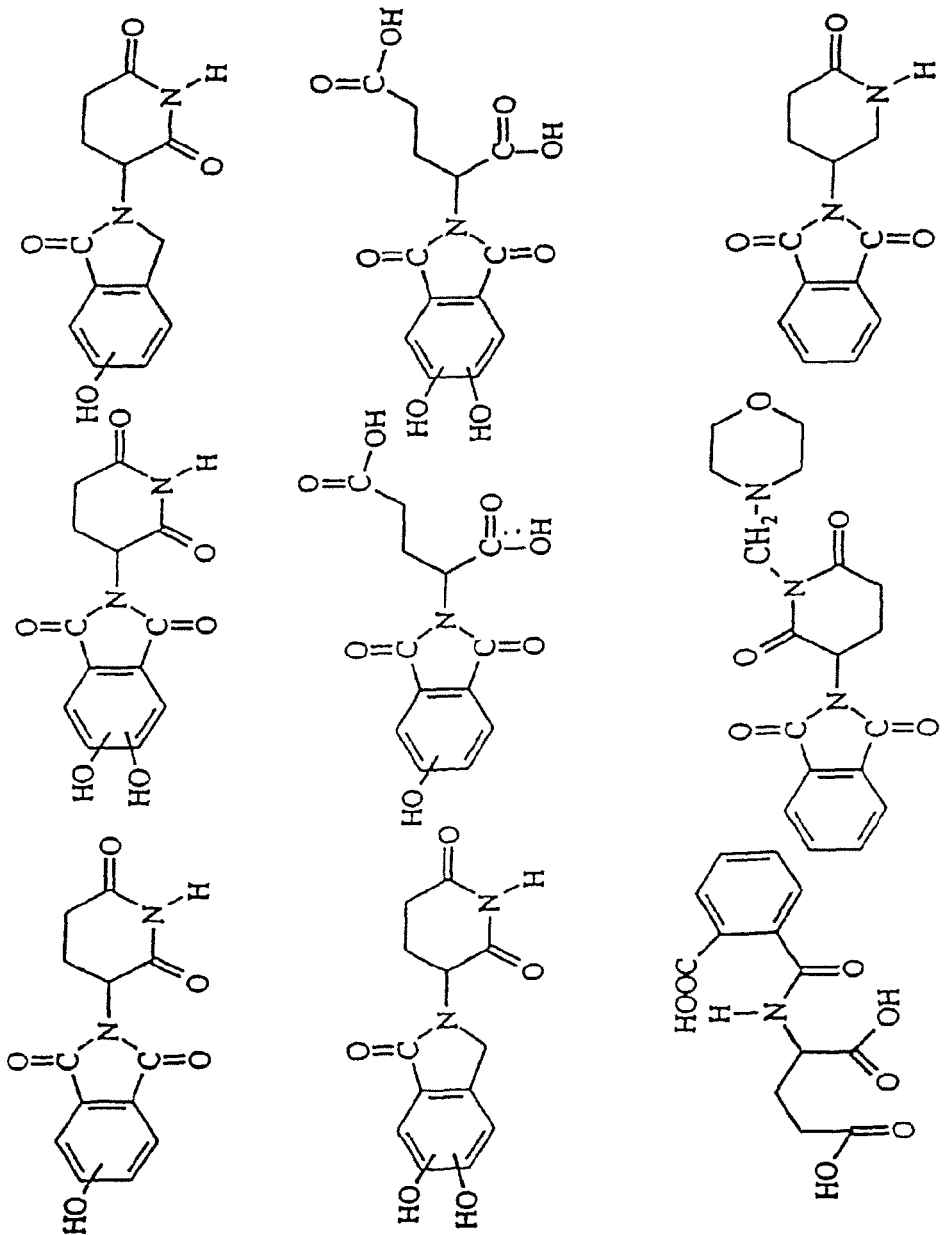

In preferred embodiments, the compound has formula B), where $R_5$ and $R_6$ are selected from the group consisting of:

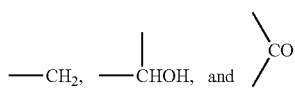

and $R_9$ has formula F) or H); and $R_{14}$ and $R_{16}$ are selected from the group consisting of:

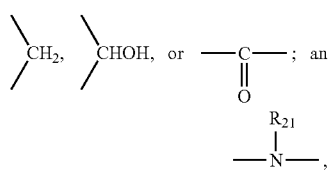

where $R_{21}$ is —H, —CH$_3$, or —OH. Specific preferred compounds according to this aspect of the present invention include thalidomide, its precursors, metabolites and analogs. Particular analogs include EM-12, N-phthaloyl-DL-glutamic acid (PGA) or N-phthaloyl-DL-glutamine anhydride. Examples of compounds that are members of this genus are listed in FIGS. 1 through 3. It is to be understood that the compounds included as part of the present invention are not to be limited to those compounds shown in FIGS. 1 through 3 and include all other compounds that are members of the genus described by the general formulas herein.

Compounds of the following formula that have anti-angiogenic properties:

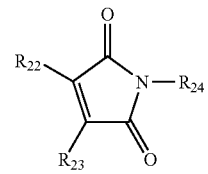

where $R_{22}$ and $R_{23}$ are (independently), —H, —F, —Cl, —Br, —I, —CH$_3$, or —CH$_2$—CH$_3$; and $R_{24}$ is —H, —CH$_3$, or —CH$_2$—CH$_3$.

The present invention also features inhibiting angiogenesis in a mammal by administering a compound according to the above formulae in a dosage sufficient to inhibit angiogenesis. Examples of specific compounds that are members of this genus are listed in FIG. 4.

Angiogenesis inhibition hydrolysis products of thalidomide having the following general formula can be used in practicing the present invention:

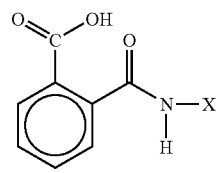

where X is $R_6$ as defined above, or

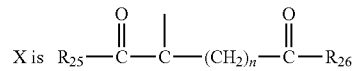

and $R_{25}$ and $R_{26}$ are, independently, —OH, —H, or NH$_2$, and n=1 through 4. Examples of such compounds are shown in FIG. 5.

Angiogenesis inhibition compounds having the following general formula can be used in practicing the present invention:

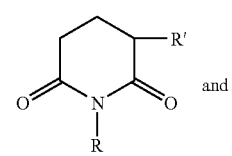
(I)

and

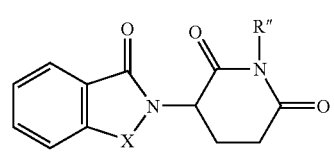
(II)

wherein R is selected from the group consisting of hydrogen, alkyl radicals of 1 to 6 carbon atoms, the phenyl radical, and the benzyl radical; wherein R' is selected from the group consisting of the phthalimido radical and the succinimido radical; wherein X is CH$_2$ or C=O; and wherein R" is H, —CH$_2$CH$_3$, —C$_6$H$_5$,

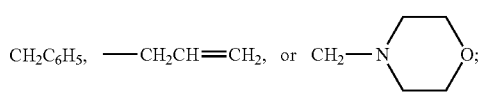

and hydrolysis products of the compounds wherein R" is H and the piperidino ring or both the piperidino and the imido ring are hydrolyzed.

Another set of compounds that are considered part of the present invention are the epoxides of thalidomide, EM-12 and EM-138. Representative epoxide compounds are shown as follows:

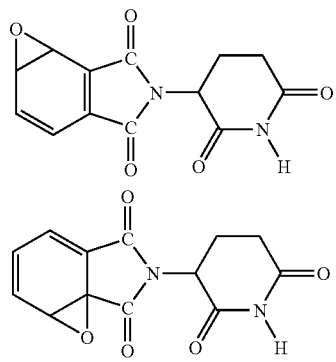
Epoxides of thalidomide

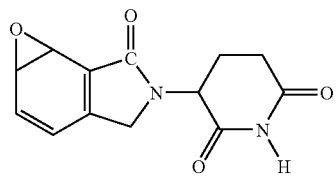
Epoxides of EM 12

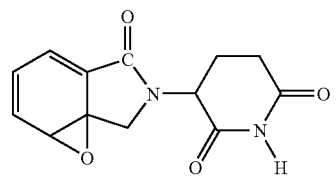

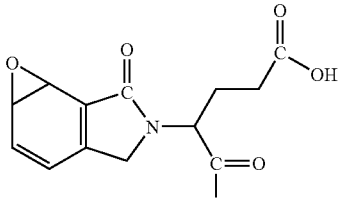

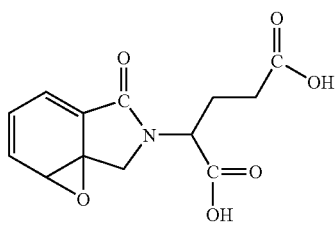
Epoxides of EM 138

It should be understood that the epoxide can be attached at the 6,1 site on the benzene ring, the 1,2 site, the 2,3 site 3,4 or the 4,5 site. All of these compounds are contemplated as part of the present invention.

The epoxides of the thalidomide, EM-12, and EM-138 can be hydrolyzed to the following compounds:

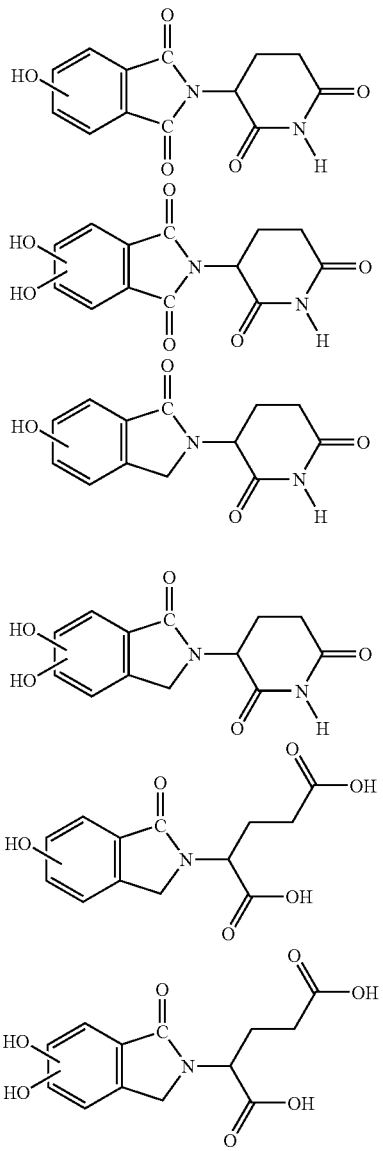

It is to be understood that the hydroxyl group can be on carbons 1, 2, 3, 4, 5 and 6 of the benzene ring. Also contemplated as part of the present invention are dihydroxyl compounds wherein the two hydroxyl groups are located bis to each other on carbons 1, 2, 3, 5 and 6 of the above compounds. The epoxides, the hydrolysis products of the epoxides, and the hydrolysis products of the thalidomide are all contemplated to be part of the present invention.

It is known that epoxides are hydrolized by a group of enzymes known as epoxide hydrolases. There is a class of compounds which are epoxide hydrolase inhibitors. Examples of these compounds are valpromide (2-propylpentanamide) and valproic acid (2-propylpentanoic acid). Because epoxides are important angiogenesis inhibitors, it is contemplated as part of the present invention, compositions comprising any of the angiogenesis inhibitors compounds recited herein in combination with epoxide hydrolase inhibitors. The epoxide hydrolase inhibitors can be administered to a human or animal together or sequentially. The epoxide group appears to be an important substituent common to several angiogenesis inhibitors. The use of epoxide hydrolase inhibitors to potentiate the activity of any angiogenesis inhibitor containing an epoxide is contemplated as part of the present invention. For example, the epoxide hydrolase inhibitors can be administered with the following epoxide-containing anti-angiogenesis compounds: AGM 1470, Eponimycin, microbial metabolites of *Scolecobasidium arenarium* designated f/2015, fr/111142 and fr/18487. See Oikawa, *Biochem Biophys. Res. Comm*, Vol. 81:1070 (1971) and Otsuka, *J. Microbial. Biotech.*, Vol 1:163 (1991).

It is contemplated as an embodiment of the present invention the use of the epoxide containing angiogenesis inhibitors with or without epoxide hydrolase inhibitors as a treatment for diseases mediated by elevated or toxic levels of TNF-a. TNF-a has been recognized as manifesting a dose dependent toxicity. If present at low levels for a long period of time, TNF-a can result in cachexia. Cachexia is a general weight loss and wasting occurring in the course of some chronic diseases such as cancer, opportunistic infections of AIDS, inflammatory diseases, parasitic diseases, tuberculosis, and high dose IL-2 therapy. The epoxide containing angiogenesis inhibitors, with or without epoxide hydrolase inhibitors, are also effective in treating diseases such as septic shock, leprosy and graph vs. host disease.

Other embodiments are within the present invention. For example, other dysmelia-causing compounds can be used according to the present invention, e.g. 4-methylphthalic acid, pyridoxine, vasopressin, acetazolamide, or a compound having the following formula (where R=H, —OH, or —CH$_3$):

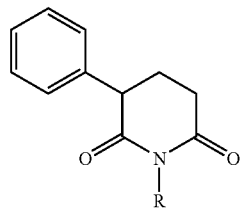

Other compounds which are teratogens, such as valproic acid (2-propylpentanoic acid), the retinoids, such as cis-retinoic acid, and rifampin may also be used in accordance with the invention.

In summary, the preferred compounds are thalidomide, as well as analogs, hydrolysis products, metabolites and precursors of thalidomide that are teratogenic, and, more specifically, that cause dysmelia. However, it is to be understood that it is not necessary for a compound to have both teratogenic activity and angiogenesis inhibiting activity to be considered part of the present invention. Dysmelia-causing compounds can be identified by the general procedures of Helm, *Arzneimittleforschung*, 31(i/6):941-949 (1981), in which rabbit pups are examined after exposure to the compound in utero. The compounds can generally be purchased, e.g., from Andrulis Pharmaceuticals, Beltsville, Md., or synthesized according to known procedures. It is to be understood that the compounds of the present invention can exist as enantiomers and that the racemic mixture of enantiomers or the isolated enantiomers are all considered as within the scope of the present invention.

Many of the compounds that are contemplated as part of the present invention can be enriched in optically active enantiomers of the compounds specified above. Specifically, Blaschke has reported that the S enantiomers may be disproportionately responsible for the dysmelia-producing effect of these compounds. See, generally Blaschke, *Arzneimittelforschung* 29:1640-1642 (1979). The above described articles generally describe procedures to obtain optically active preparations of the compounds of interest. See, e.g. Shealy et al., *Chem. Indus.* 1030 (1965); and Casini et al., *Farmaco Ed. Sci.* 19:563 (1964).

In another embodiment, the invention also includes the inhibition of angiogenesis and the treatment of angiogenesis dependent diseases by administering antiinflammatory compounds, either alone or in combination with other angiogenesis inhibiting compounds, such as those described above. These antiinflammatory compounds may be either steroids or nonsteroidal antiinflammatory drugs (NSAIDs). Examples of steroids which may be used in the invention include, but are not limited to, cortisone, cortisol, corticosterone, hydrocortisone, hydrocortisol, prednisone, prednisolone, dexamethasone, beclomethasone, betamethasone, mometasone, mometasone furoate, budesonide, triamcinolone acetonide, and fluticasone. Preferred steroids are prednisone, hydrocortisone, cortisol, dexamethasone, betamethasone, and beclomethasone. Especially preferred steroids are hydrocortisone, dexamethasone, and betamethasone.

Examples of NSAIDs which may be used in the invention include, but are not limited to, aspirin, acetominophen, ibuprofen, esculetin, phenidone, quercetin, ketoprofen, nordihydroguiaretic acid (NDGA), sulindac, sulindac sulfone, sulindac sulfide, indomethacin, NS-398 (a cyclooxygenase-2 inhibitor), cyclooxygenase-1 inhibitors, methylheptyl imidazole, furegrelate sodium, SKF525AHCL, thromboxane inhibitors, toradol, ecasa, salsalate, diflunisal, mefenamic acid, naproxen, naproxen sodium, floctafenine, meclofenamate, phenylbutazone, oxyphenbutazone, diclofenac, etodolac, fenoprofen, flufenamic acid, flurbiprofen, pirprofen, tolmetin, apazone, fenbufen, nabumetone, oxaprozin, piroxicam, salicylate, and tenoxicam. Preferred NSAIDs are sulindac, sulindac sulfone, sulindac sulfide, indomethacin, NS-398, methylheptyl imidazole, furegrelate sodium, and SKF525AHCL. Especially preferred NSAIDs are indomethacin and sulindac.

Sulindac, which includes (Z)-5-Fluoro-2-methyl-1-[[4-(methyl-sulfinyl)phenyl]methylene]-1H-indene-3-acetic acid, or cis-5-fluoro-2-methyl-1-[p-(methylsulfinyl)benzylidene]indene-3-acetic acid, has the following structure:

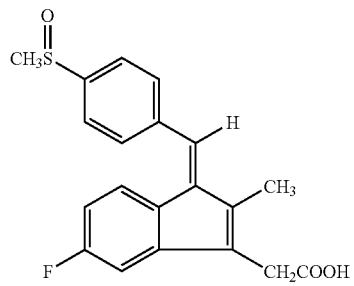

Such compounds can be used to treat angiogenesis dependent diseases. Such compounds can be used alone or in combination with other angiogenesis inhibiting compounds to treat angiogenesis dependent diseases, such as cancer.

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441-446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, radial keratotomy, pemphigoid and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and, thus, maintain the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, non-specific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus, reducing the influx of inflammatory cells and the lesion formation.

Sarcoidosis is another chronic inflammatory disease that is characterized as a multisystem granulomatous disorder. The granulomas of this disease may form anywhere in the body, and, thus, the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated according to the present invention are hemangiomas, Osler-Weber-Rendu disease, or hereditary hemorrhagic telangiectasia, solid or blood borne tumors and acquired immune deficiency syndrome.

The compositions and methods of the present invention include the use of angiogenesis inhibiting compounds and antiinflammatory compounds, such as steroids or nonsteroidal antiinflammatory drugs (NSAIDs). The compositions and methods of the present invention include the combination of angiogenesis inhibiting compounds, such as thalidomide or thalidomide-like analogs or AMG-1470, EM-12 or EM-138 with antiinflammatory compounds, such as steroids or non-steroidal antiinflammatory drugs (NSAIDs). The compositions and methods of the present invention also include the use antiinflammatory compounds alone. These compositions can be used to treat angiogenesis dependent diseases.

For example, it has been found that indomethacin (5 mg/kg) inhibits bFGF induced angiogenesis by 59% and VEGF induced angiogenesis by 61%. Similarly, sulindac (25 mg/kg) has been found to inhibit bFGF induced angiogenesis by 50% and VEGF induced angiogenesis by 55%. Sulindac is metabolized in vivo to two metabolites: sulindac sulfide and sulindac sulfone. Sulindac sulfide actively inhibits prostaglandin synthesis, while sulindac sulfone does not; however, both were found to be inhibitors of angiogenesis. Sulindac sulfide was found to inhibit bFGF induced neovascularization by 34%, and sulindac sulfone exhibited 31% inhibition.

Other NSAIDs have also been found to inhibit angiogenesis associated neovascularization. For example, carbomethylheptyl imidazole and furegrelate sodium, both thromboxane inhibitors, inhibit bFGF induced neovascularization 32% and 22%, respectively. Another thromboxane inhibitor, SKF525AHCL, which promotes prostaglandin production, was found to inhibit bFGF induced neovascularization by 25%. The specific cyclooxygenase-2 inhibitor NS-398 also inhibited bFGF induced neovascularization by 25%.

When sulindac is combined with thalidomide, there is an additive effect in the inhibition of angiogenesis. When sulindac is combined with other angiogenesis inhibiting compounds, such as AMG 1470, EM-12 or EM-138, there is an additive effect in the inhibition of angiogenesis. Angiogenesis in the eye, in the assay described in Example 2, is produced by the presence of bFGF (basic fibroblastic growth factor) and VEGF (vascular endothelial cell growth factor). Inhibition of such angiogenesis was shown with the NSAIDs, steroids, thalidomide, or the combination of thalidomide and an NSAID, sulindac.

| AGENT | DOSE | bFGF[1] | VEGF[2] |
|---|---|---|---|
| Aspirin | 100 mg/kg | 8 | — |
| Acetaminophen | 100 mg/kg | 0 | 0 |

-continued

| AGENT | DOSE | bFGF[1] | VEGF[2] |
|---|---|---|---|
| Ibuprofen | 20 mg/kg | 7 | 11 |
| Hydrocortisone | 20 mg/kg | 50 | 40 |
| Sulindac | 25 mg/kg | 52 | 54 |
| Thalidomide | 200 mg/kg | 42 | 44 |
| Thalidomide + Sulindac | 200 mg/kg (thal) + 25 mg/kg (sulindac) | 65 | 74 |
| AGM 1470 | 30 mg/kg qod | 48 | |
| AGM 1470 + Sulindac | 30 mg/kg qod (AGM) + 25 mg/kg (sulindac) | 70 | |

[1] % Inhibition of bFGF induced angiogenesis
[2] % Inhibition of VEGF induced angiogenesis The inhibition of VEGF by 74% demonstrates the additive effect when thalidomide and sulindac are combined. The data for hydrocortisone, sulindac, thalidomide and thalidomide+sulindac differ significantly from the controls (p<0.0001). Studies with the composition comprising thalidomide and sulindac on V2 carcinoma in rabbits has demonstrated a T/C (treated to control ratio) of 0.32 after 18 days of oral treatment with thalidomide 200 mg/kg combined with 25 mg/kg sulindac.

An additive effect is also seen in the combination of non-steriodal antiinflammatory drugs and other angiogenesis inhibiting compounds such as the combination of sulindac and AMG-1470. AGM-1470 is a known angiogenesis inhibiting compound as shown in Brem et al. Minimal drug resistance occurs after prolonged antiangiogenic therapy with AGM-1470, *Surgical Forum* 45 (0), 1994, pp 674-677, herein incorporated by reference. As shown in the above chart, sulindac plus AGM-1470 shows a greater inhibitory effect upon angiogenesis than does either compound alone.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example I

The chick embryo chorioallantoic membrane assay described by Crum et al., *Science* 230:1375 et seq. (1985), is used to identify compounds that do not require further metabolic conversion. See also, U.S. Pat. No. 5,001,116, hereby incorporated by reference, which describes the CAM assay at col. 7 of the patent. Briefly, fertilized chick embryos were removed from their shell on day 3 or 4, and a methylcellulose disc containing the compound was implanted on the chorioallantoic membrane. The embryos were examined 48 hours later and, if a clear avascular zone appeared around the methylcellulose disc, the diameter of that zone was measured.

Example II

Rabbit Cornea Angiogenesis Assay

Pellets for implantation into rabbit corneas were made by mixing 110 µl of saline containing 12 µg of recombinant bFGF (Takeda Pharmaceuticals-Japan) with 40 mg of sucralfate (Bukh Meditec-Denmark); this suspension was added to 80 µl of 12% hydron (Interferon Sciences) in ethanol. 10 µl aliquots of this mixture was then pipetted onto Teflon pegs and allowed to dry producing approximately 17 pellets. A pellet was implanted into corneal micropockets of each eye of an anesthetized female New Zealand white rabbit, 2 mm from the limbus followed by topical application of erythromycin ointment onto the surface of the cornea. The animals were fed daily from 2 days post-implantation by gastric lavage with either drug suspended in 0.5% carboxymethyl cellulose or 0.5% carboxymethyl cellulose alone. Thalidomide was purchased from Andrulus Pharmaceutical (Maryland) and the EM-12 and Supidimide were kindly provided by Grunenthal GMBH (Germany). The animals were examined with a slit lamp every other day in a masked manner by the same corneal specialist. The area of corneal neovascularization was determined by measuring with a reticule the vessel length (L) from the limbus and the number of clock hours (C) of limbus involved. A formula was used to determine the area of a circular band segment: $C/12*3.1416 [r^2-(r-L)^2]$ where r=6 mm the measured radius of the rabbit cornea. Various mathematical models were utilized to determine the amount of vascularized cornea, and this formula was found to provide the most accurate approximation of the area of the band of neovascularization that grows towards the pellet.

It is important to note that the rabbit cornea assay is preferable because it will generally recognize compounds that are inactive per se but are metabolized to yield active compounds. Thalidomide related compounds, as shown below in Example III, are known to be teratogens and are candidates for use in the present invention.

Example III

Inhibition of bFGF Induced Corneal Neovascularization by Thalidomide and Related Analog Expressed as Percent of Median Control on Day 8

Pellets containing bFGF and sucralfate were implanted into micropockets of both corneas of rabbits according to Example II. Vessel ingrowth into clear cornea from the limbus was first noted on day 2 and treatments (200 mg/kg orally) were begun on this day. The area of corneal neovascularization was measured from day 4 through day 12. Day 8 measurements were used for comparison between groups. No regression of vessels and near maximal neovascularization was seen at this time point. Statistical analysis was performed with ANOVA with ranked data to account for interexperimental variation and to guard against a non-normal distribution of data (i.e. outliers) by utilizing a nonparametric method.

The compounds tested were as follows:

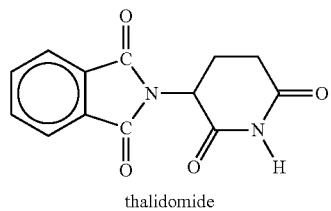
thalidomide

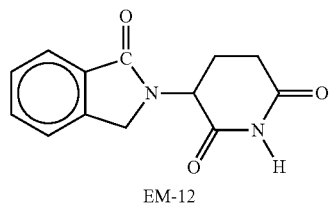
EM-12

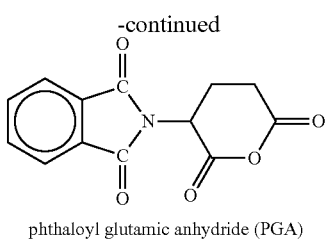

phthaloyl glutamic anhydride (PGA)

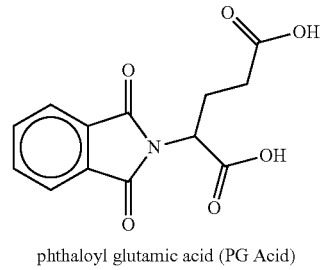

phthaloyl glutamic acid (PG Acid)

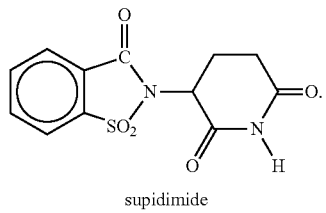

supidimide

Treatment with a dose of (200 mg/kg) of thalidomide resulted in an inhibition of the area of vascularized cornea that ranged from 30-51% in three experiments with a median inhibition of 36% (FIG. 6) (n=30 eyes, p=0.0001, 2 way ANOVA with ranked data). The inhibition of angiogenesis by thalidomide was seen after only two doses (FIG. 7). The rabbits did not demonstrate obvious sedation and there were no signs of toxicity or weight loss. The teratogenic analog EM-12, which shares the other properties of thalidomide was also inhibitory, with a median inhibition of 42% (n=10 eyes, p=0.002, 1-way ANOVA with ranked data). Supidimide, a nonteratogenic analog of thalidomide that retains the sedative properties of thalidomide, exhibited no activity (area 107% of control, n=10 eyes, not statistically different from control). Other analogs, PGA and PG acid displayed weaker inhibitory effects than thalidomide (data not shown). The density of vessel ingrowth in thalidomide-treated animals was also markedly reduced.

Example IV

EM-12 in Rabbit Cornea Assay

EM-12 was tested in the rabbit cornea assay described in Example II at 100 mg/kg/day and showed 21% inhibition, and at 200 mg/kg/day the assay showed 43% inhibition.

Example V

Phthaloyl Glutamic Acid in CAM

Phthaloyl glutamic acid was tested in the above described CAM assay and exhibit an avascular zone with a mild scar.

Example VI

Phthaloyl Glutamic Acid in Rabbit Cornea Assay

Phthaloyl glutamic acid described above at 200 mg/kg and exhibited 29% inhibition of angiogenesis.

Example VII

Phthaloyl Glutamic Anhydride in CAM Assay

Phthaloyl glutamic anhydride was test in the CAM assay described above and exhibited an avascular zone.

Example VIII

Treatment of Crohn's Disease

A 32 year old female patient with Crohn's disease was treated using the methods of the present invention. The patient exhibited the characteristic symptoms of Crohn's disease, i.e., severe gastrointestinal involvement (including diarrhea and cramping) and a large skin lesion on the lower leg. Thalidomide was orally administered to her at a dosage of 100 mg twice a day. After treatment was continued for one week, the gastrointestinal symptoms, including the diarrhea and cramping, were lessened and the skin lesion resolved.

Example IX

Corneal Micropocket Assay

Six to eight week old C57B 16 male mice were obtained from Jackson Laboratories, MA. The mice were anesthetized, and 0.4×0.4 mm pockets were made in the stroma of the mouse cornea adjacent to the limbus. Pellets containing 80 ng of either bFGF or VEGF were implanted in the pellets. The pellets containing bFGF were implanted 1.0-1.2 mm from the limbal vessels, while the pellets containing VEGF were implanted 0.5-0.7 mm from the limbal vessels. Erythromycin was then topically applied.

The mice were then treated with varying doses of antiinflammatory drugs as shown in the table below. The vascular response to the pellets was measured by maximal vessel length and number of clock hours of neovascularization 5 days after implantation of the bFGF pellets and 6 days after implantation of the VEGF pellets. The area of corneal neovascularization was calculated using the following formula which best approximated the area of neovascularization: Area $(mm^2) = [\pi \times clock\ hours \times length\ (mm) \times 0.2\ (mm)]$. The results are shown in the following table.

| AGENT | DOSE | bFGF[1] | VEGF[2] | n | p-value |
|---|---|---|---|---|---|
| Acetaminophen | 100 mg/kg | 0 | — | 8 | ns |
| Aspirin | 10-160 mg/kg | 0-11 | — | 8 | ns |
| NDGA | 25 mg/kg | 30 | — | 8 | ns |
| Esculetin | 200 mg/kg | 15 | — | 8 | .02 |
| Phenidone | 100 mg/kg | 17 | — | 8 | <.01 |
| Quercetin | 300 mg/kg | 18 | — | 8 | <.01 |
| Ibuprofen | 25 mg/kg | 6 | 8 | 23/8 | ns/ns |
| Ketoprofen | 80 mg/kg | 30 | 41 | 8/8 | <.01 |
| Indomethacin | 5 mg/kg | 59 | 61 | 15/21 | <.01/<.01 |
| Sulindac | 25 mg/kg | 50 | 55 | 15/15 | <.01/<.01 |

[1] % Inhibition of bFGF induced angiogenesis
[2] % Inhibition of VEGF induced angiogenesis Inhibitory effect is expressed in percentage representing the area of corneal neovascularization by either bFGF or VEGF compared to controls (n=8/experiment) of the experiments in which that particular drug was tested. N=the number of eyes that were tested and drugs were given once daily either sc, ip or oral as described.

Example X

Six to eight week old C57B 16 male mice were obtained from Jackson Laboratories, MA. The mice were anesthetized, and 0.4×0.4 mm pockets were made in the stroma of the mouse cornea adjacent to the limbus. Pellets containing 80 ng of either bFGF or VEGF were implanted. The pellets containing bFGF were implanted 1.0-1.2 mm from the limbal vessels, while the pellets containing VEGF were implanted 0.5-0.7 mm from the limbal vessels. Erythromycin was then topically applied.

The mice were then treated with thalidomide, indomethacin, sulindac, or combinations of thalidomide with either indomethacin or sulindac. The vascular response to the pellets was measured by maximal vessel length and number of clock hours of neovascularization 5 days after implantation of the bFGF pellets and 6 days after implantation of the VEGF pellets. The area of corneal neovascularization was calculated using the following formula which best approximates the area of neovascularization: Area $(mm^2)=[\pi \times clock\ hours \times length\ (mm) \times 0.2\ (mm)]$. The results are shown in the following table.

| AGENT | DOSE | bFGF[1] | VEGF[2] | n |
|---|---|---|---|---|
| Thalidomide | 200 mg/kg | 41 | 40 | 31/39 |
| Indomethacin | 5 mg/kg | 59 | 61 | 15/21 |
| Sulindac | 25 mg/kg | 50 | 55 | 15/15 |
| Thalidomide + Indomethacin | 200 mg/kg + 5 mg/kg | 67 | 61 | 15/21 |
| Thalidomide + Sulindac | 200 mg/kg + 25 mg/kg | 63[3] | 74[3] | 15/16 |

[1]% Inhibition of bFGF induced angiogenesis
[2]% Inhibition of VEGF induced angiogenesis
[3]Inhibitory effect is significantly different from either agent alone (p < .01, tested by ANOVA)

Inhibitory effect is expressed in percentage representing the area of corneal neovascularization by either bFGF or VEGF compared to controls (n=8/experiment) of the experiments in which that particular drug was tested. N=the number of eyes that were tested and drugs were given once daily either sc, ip or oral as described.

Example XI

Six to eight week old C57B16 male mice, obtained from Jackson Laboratories, MA, were anesthetized, and 0.4×0.4 mm pockets were made in the stroma of the mouse cornea adjacent to the limbus. Pellets containing 80 ng of bFGF were implanted 1.0-1.2 mm from the limbal vessels. Erythromycin was then topically applied.

The mice were then treated with sulindac, or one of the sulindac derivatives, sulindac sulfone or sulindac sulfide. The vascular response to the pellets was measured by maximal vessel length and number of clock hours of neovascularization 5 days after implantation of the bFGF pellets. The area of corneal neovascularization was calculated using the following formula which best approximates the area of neovascularization: Area $(mm^2)=[\pi \times clock\ hours \times length\ (mm) \times 0.2\ (mm)]$. The results are shown in the following table.

| AGENT | DOSE | % inhibition | n |
|---|---|---|---|
| Sulindac | 25 mg/kg | 50 | 15 |
| Sulindac sulfide | 25 mg/kg | 31 | 8 |
|  | 50 mg/kg | 34 | 8 |
| Sulindac sulfone | 25 mg/kg | 31 | 16 |

Inhibitory effect is expressed in percentage representing the area of corneal neovascularization by bFGF compared to controls (n=8/experiment. N=the number of eyes that were tested and drugs were given once daily either sc, ip or oral as described.

Example XII

Tumor Assay

New Zealand White female rabbits, weighing approximately 1.5 kg, obtained from Charles River, Mass., were used for propagating the V2-carcinoma. This tumor originates from a Shope virus-induced papilloma. Small 0.5×0.5 cm pieces were implanted intramuscularly in the right thigh. Treatment with 200 mg/kg/day thalidomide (n=14), 60 mg/kg/day sulindac (n=5), or a combination of thalidomide and sulindac (n=10) was started at day 10 after tumor implantation, when the mean volume of the tumor was 6 cm$^3$. The control animals (n=13) were treated with methylcellulose. The rabbits were sacrificed 17 days after the start of treatment when mean volume of the control tumors was 100 cm$^3$. The results of this experiment (FIG. 8) show that the combination of thalidomide and sulindac is more effective in reducing the size of V2-carcinoma tumors than either thalidomide or sulindac alone. The combination of thalidomide and sulindac inhibited tumor growth by 75% and was significantly different (p<0.05) from either agent alone or the control group. Oral treatment with sulindac or thalidomide inhibited tumor growth by, respectively, 35% (n=5, p<0.01) and 55% (n=14, p<0.01). The data were collected in 3 separate experiments and each bar represents the standard error of the mean.

It should be understood, of course, that the foregoing relates only to preferred embodiments of the present invention and that numerous modifications or alterations may be made therein without departing from the spirit and the scope of the invention as set forth in the appended claims.

I claim:

1. A method of treating a blood-borne tumor comprising administering to a patient having a blood-borne tumor who had no prior treatment for the tumor an effective amount of thalidomide and an amount of prednisone.

2. The method of claim 1, wherein the blood-borne tumor is leukemia.

3. The method of claim 1, wherein the amount of thalidomide administered is from 0.1 to 50 mg/kg/day.

4. The method of claim 3, wherein the amount of thalidomide administered is from 0.5 to 50 mg/kg/day.

5. The method of claim 4, wherein the amount of thalidomide administered is from 1 to 10 mg/kg/day.

6. The method of claim 1, wherein at least one of thalidomide and prednisone is parenterally administered.

7. The method of claim 1, wherein at least one of thalidomide and prednisone is orally administered.

8. The method of claim 1, wherein the thalidomide and prednisone are simultaneously administered.

9. The method of claim 1, wherein the thalidomide and prednisone are sequentially administered.

10. The method of claim 1, further comprising administration of an additional angiogenesis inhibiting compound.

* * * * *